(12) United States Patent
Nae et al.

(10) Patent No.: US 11,865,282 B2
(45) Date of Patent: Jan. 9, 2024

(54) SYSTEMS AND METHODS FOR CREATING AN INTERATRIAL SHUNT

(71) Applicant: V-Wave Ltd., Caesarea (IL)

(72) Inventors: Nir Nae, Binyamina (IL); Tal Weisinger, Haifa (IL); Lior Rosen, Or Akiva (IL); James Whiting, Los Angeles, CA (US); Neal Eigler, Agoura Hills, CA (US); Werner Hafelfinger, Thousand Oaks, CA (US); Erez Rozenfeld, Shoham (IL)

(73) Assignee: V-Wave Ltd., Caesarea (IL)

( * ) Notice: Subject to any disclaimer, the term of this patent is extended or adjusted under 35 U.S.C. 154(b) by 899 days.

(21) Appl. No.: 16/876,640

(22) Filed: May 18, 2020

(65) Prior Publication Data

US 2020/0368505 A1    Nov. 26, 2020

Related U.S. Application Data

(60) Provisional application No. 62/850,511, filed on May 20, 2019.

(51) Int. Cl.
*A61M 27/00* (2006.01)
*A61B 18/14* (2006.01)
(Continued)

(52) U.S. Cl.
CPC ....... *A61M 27/002* (2013.01); *A61B 18/1492* (2013.01); *A61M 25/1011* (2013.01);
(Continued)

(58) Field of Classification Search
None
See application file for complete search history.

(56) References Cited

U.S. PATENT DOCUMENTS 3,852,334 A   12/1974   Dusza et al.
3,874,388 A    4/1975   King et al.
(Continued)

FOREIGN PATENT DOCUMENTS

AU   2003291117 B2   4/2009
CA      2378920 A1   2/2001
(Continued)

OTHER PUBLICATIONS

U.S. Appl. No. 09/839,643, U.S. Pat. No. 8,091,556, filed Apr. 20, 2001, Jan. 10, 2012.
(Continued)

*Primary Examiner* — Jon Eric C Morales
(74) *Attorney, Agent, or Firm* — Eversheds Sutherland (US) LLP; Christopher C. Bolten; Albert K. Heng

(57) ABSTRACT

A device for precise control of blood flow across an interatrial septum is provided. The device includes a sheath having a first set of openings disposed within a first atrium while a second set of openings is disposed within a second atrium. An actuator may be actuated to move an inner sleeve within the sheath to modify the area of second set of openings to permit blood to flow between the first and second atria responsive to a pressure gradient across the interatrial septum via the first and second openings at a blood flow rate corresponding with the area of the second set of openings of the sheath. In addition, the patient's hemodynamics responsive to the shunting of blood across the interatrial septum at each incremental area of the opening may be monitored for selecting a specific sized implantable interatrial shunt for the patient.

27 Claims, 17 Drawing Sheets

(51) Int. Cl.
*A61M 25/10* (2013.01)
*A61B 18/00* (2006.01)
*A61M 25/09* (2006.01)

(52) U.S. Cl.
CPC ............... *A61B 2018/0022* (2013.01); *A61B 2018/0038* (2013.01); *A61B 2018/00577* (2013.01); *A61M 25/09* (2013.01); *A61M 2205/3331* (2013.01); *A61M 2205/3334* (2013.01); *A61M 2210/125* (2013.01); *A61M 2230/20* (2013.01); *A61M 2230/205* (2013.01); *A61M 2230/30* (2013.01)

(56) References Cited

U.S. PATENT DOCUMENTS

| | | |
|---|---|---|
| 3,952,334 A | 4/1976 | Bokros et al. |
| 4,364,395 A | 12/1982 | Redmond et al. |
| 4,484,955 A | 11/1984 | Hochstein |
| 4,601,309 A | 7/1986 | Chang |
| 4,617,932 A | 10/1986 | Kornberg |
| 4,662,355 A | 5/1987 | Pieronne et al. |
| 4,665,906 A | 5/1987 | Jervis |
| 4,705,507 A | 11/1987 | Boyles |
| 4,836,204 A | 6/1989 | Landymore et al. |
| 4,979,955 A | 12/1990 | Smith |
| 4,988,339 A | 1/1991 | Vadher |
| 4,995,857 A | 2/1991 | Arnold |
| 5,035,702 A | 7/1991 | Taheri |
| 5,035,706 A | 7/1991 | Giantureo et al. |
| 5,037,427 A | 8/1991 | Harada et al. |
| 5,089,005 A | 2/1992 | Harada |
| 5,186,431 A | 2/1993 | Tamari |
| 5,197,978 A | 3/1993 | Hess |
| 5,234,447 A | 8/1993 | Kaster et al. |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,378,239 A | 1/1995 | Termin et al. |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,545,210 A | 8/1996 | Hess et al. |
| 5,556,386 A | 9/1996 | Todd |
| 5,578,008 A | 11/1996 | Hara |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,324 A | 4/1998 | Glastra |
| 5,749,880 A | 5/1998 | Banas et al. |
| 5,779,716 A | 7/1998 | Cano et al. |
| 5,795,307 A | 8/1998 | Krueger |
| 5,810,836 A | 9/1998 | Hussein et al. |
| 5,824,062 A | 10/1998 | Patke et al. |
| 5,824,071 A | 10/1998 | Nelson et al. |
| 5,846,261 A | 12/1998 | Kotula et al. |
| 5,910,144 A | 6/1999 | Hayashi |
| 5,916,193 A | 6/1999 | Stevens et al. |
| 5,941,850 A | 8/1999 | Shah et al. |
| 5,957,949 A | 9/1999 | Leonhardt et al. |
| 5,990,379 A | 11/1999 | Gregory |
| 6,007,544 A | 12/1999 | Kim |
| 6,027,518 A | 2/2000 | Gaber |
| 6,039,755 A | 3/2000 | Edwin et al. |
| 6,039,759 A | 3/2000 | Carpentier et al. |
| 6,086,610 A | 7/2000 | Duerig et al. |
| 6,111,520 A | 8/2000 | Allen et al. |
| 6,117,159 A | 9/2000 | Huebsch et al. |
| 6,120,534 A | 9/2000 | Ruiz |
| 6,124,523 A | 9/2000 | Banas et al. |
| 6,126,686 A | 10/2000 | Badylak et al. |
| 6,165,188 A | 12/2000 | Saadat et al. |
| 6,210,318 B1 | 4/2001 | Lederman |
| 6,214,029 B1 | 4/2001 | Thill et al. |
| 6,214,039 B1 | 4/2001 | Banas et al. |
| 6,217,541 B1 | 4/2001 | Yu |
| 6,221,096 B1 | 4/2001 | Aiba et al. |
| 6,231,587 B1 | 5/2001 | Makower |
| 6,242,762 B1 | 6/2001 | Brown et al. |
| 6,245,099 B1 | 6/2001 | Edwin et al. |
| 6,254,564 B1 | 7/2001 | Wilk et al. |
| 6,260,552 B1 | 7/2001 | Mortier et al. |
| 6,264,684 B1 | 7/2001 | Banas et al. |
| 6,270,515 B1 | 8/2001 | Linden et al. |
| 6,270,526 B1 | 8/2001 | Cox |
| 6,277,078 B1 | 8/2001 | Porat et al. |
| 6,278,379 B1 | 8/2001 | Allen et al. |
| 6,290,728 B1 | 9/2001 | Phelps et al. |
| 6,302,892 B1 | 10/2001 | Wilk |
| 6,306,141 B1 | 10/2001 | Jervis |
| 6,328,699 B1 | 12/2001 | Eigler et al. |
| 6,344,022 B1 | 2/2002 | Jarvik |
| 6,358,277 B1 | 3/2002 | Duran |
| 6,391,036 B1 | 5/2002 | Berg et al. |
| 6,398,803 B1 | 6/2002 | Layne et al. |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,475,136 B1 | 11/2002 | Forsell |
| 6,478,776 B1 | 11/2002 | Rosenman et al. |
| 6,485,507 B1 | 11/2002 | Walak et al. |
| 6,488,702 B1 | 12/2002 | Besselink |
| 6,491,705 B2 | 12/2002 | Gifford et al. |
| 6,527,698 B1 | 3/2003 | Kung et al. |
| 6,544,208 B2 | 4/2003 | Ethier et al. |
| 6,547,814 B2 | 4/2003 | Edwin et al. |
| 6,562,066 B1 | 5/2003 | Martin |
| 6,572,652 B2 | 6/2003 | Shaknovich |
| 6,579,314 B1 | 6/2003 | Lombardi et al. |
| 6,589,198 B1 | 7/2003 | Soltanpour et al. |
| 6,616,675 B1 | 9/2003 | Evard et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,740,115 B2 | 5/2004 | Lombardi et al. |
| 6,758,858 B2 | 7/2004 | McCrea et al. |
| 6,764,507 B2 | 7/2004 | Shanley et al. |
| 6,770,087 B2 | 8/2004 | Layne et al. |
| 6,797,217 B2 | 9/2004 | McCrea et al. |
| 6,890,350 B1 | 5/2005 | Walak et al. |
| 6,923,829 B2 | 8/2005 | Boyle et al. |
| 6,970,742 B2 | 11/2005 | Mann et al. |
| 7,001,409 B2 | 2/2006 | Amplatz |
| 7,004,966 B2 | 2/2006 | Edwin et al. |
| 7,025,777 B2 | 4/2006 | Moore |
| 7,060,150 B2 | 6/2006 | Banas et al. |
| 7,083,640 B2 | 8/2006 | Lombardi et al. |
| 7,115,095 B2 | 10/2006 | Eigler et al. |
| 7,118,600 B2 | 10/2006 | Dua et al. |
| 7,137,953 B2 | 11/2006 | Eigler et al. |
| 7,147,604 B1 | 12/2006 | Allen et al. |
| 7,149,587 B2 | 12/2006 | Wardle et al. |
| 7,169,160 B1 | 1/2007 | Middleman et al. |
| 7,169,172 B2 | 1/2007 | Levine et al. |
| 7,195,594 B2 | 3/2007 | Eigler et al. |
| 7,208,010 B2 | 4/2007 | Shanley et al. |
| 7,226,558 B2 | 6/2007 | Nieman et al. |
| 7,245,117 B1 | 7/2007 | Joy et al. |
| 7,294,115 B1 | 11/2007 | Wilk |
| 7,306,756 B2 | 12/2007 | Edwin et al. |
| 7,402,899 B1 | 7/2008 | Whiting et al. |

(56) References Cited

U.S. PATENT DOCUMENTS

| | | |
|---|---|---|
| 7,439,723 B2 | 10/2008 | Allen et al. |
| 7,468,071 B2 | 12/2008 | Edwin et al. |
| 7,483,743 B2 | 1/2009 | Mann et al. |
| 7,498,799 B2 | 3/2009 | Allen et al. |
| 7,509,169 B2 | 3/2009 | Eigler et al. |
| 7,550,978 B2 | 6/2009 | Joy et al. |
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |
| 7,679,355 B2 | 3/2010 | Allen et al. |
| 7,717,854 B2 | 5/2010 | Mann et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,216,398 B2 | 7/2012 | Bledsoe et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler et al. |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Phan et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,665,086 B2 | 3/2014 | Miller et al. |
| 8,696,611 B2 | 4/2014 | Nitzan et al. |
| 8,790,241 B2 | 7/2014 | Edwin et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 9,005,155 B2 | 4/2015 | Sugimoto |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 | 6/2015 | Gallagher et al. |
| 9,205,236 B2 | 12/2015 | McNamara et al. |
| 9,220,429 B2 | 12/2015 | Nabutovsky et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 | 9/2018 | Eigler et al. |
| 10,105,103 B2 | 10/2018 | Goldshtein et al. |
| 10,111,741 B2 | 10/2018 | Michalak |
| 10,207,087 B2 | 2/2019 | Keren et al. |
| 10,251,750 B2 | 4/2019 | Eigler et al. |
| 10,265,169 B2 | 4/2019 | Desrosiers et al. |
| 10,299,687 B2 | 5/2019 | Nabutovsky et al. |
| 10,357,320 B2 | 7/2019 | Beira |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,548,725 B2 | 2/2020 | Alkhatib et al. |
| 10,561,423 B2 | 2/2020 | Sharma |
| 10,583,002 B2 | 3/2020 | Lane et al. |
| 10,639,459 B2 | 5/2020 | Nitzan et al. |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,940,296 B2 | 3/2021 | Keren |
| 11,109,988 B2 | 9/2021 | Rosen et al. |
| 11,135,054 B2 | 10/2021 | Nitzan et al. |
| 11,234,702 B1 | 2/2022 | Eigler et al. |
| 11,253,353 B2 | 2/2022 | Levi et al. |
| 11,291,807 B2 | 4/2022 | Eigler et al. |
| 11,304,831 B2 | 4/2022 | Nae et al. |
| 2001/0021872 A1 | 9/2001 | Bailey et al. |
| 2002/0099431 A1 | 7/2002 | Armstrong et al. |
| 2002/0120277 A1 | 8/2002 | Hauschild et al. |
| 2002/0165479 A1 | 11/2002 | Wilk |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2002/0183628 A1 | 12/2002 | Reich et al. |
| 2003/0028213 A1 | 2/2003 | Thill et al. |
| 2003/0045902 A1 | 3/2003 | Weadock |
| 2003/0100920 A1 | 5/2003 | Akin et al. |
| 2003/0125798 A1 | 7/2003 | Martin |
| 2003/0136417 A1 | 7/2003 | Fonseca et al. |
| 2003/0139819 A1 | 7/2003 | Beer et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2003/0216803 A1 | 11/2003 | Ledergerber |
| 2004/0010219 A1 | 1/2004 | McCusker et al. |
| 2004/0016514 A1 | 1/2004 | Nien |
| 2004/0073242 A1 | 4/2004 | Chanduszko |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0116999 A1 | 6/2004 | Ledergerber |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0147969 A1 | 7/2004 | Mann et al. |
| 2004/0162514 A1 | 8/2004 | Alferness et al. |
| 2004/0193261 A1 | 9/2004 | Berreklouw |
| 2004/0210190 A1 | 10/2004 | Kohler et al. |

(56) References Cited

U.S. PATENT DOCUMENTS

| | | |
|---|---|---|
| 2004/0210307 A1 | 10/2004 | Khairkhahan |
| 2004/0225352 A1 | 11/2004 | Osborne et al. |
| 2005/0003327 A1 | 1/2005 | Elian et al. |
| 2005/0033327 A1 | 2/2005 | Gainor et al. |
| 2005/0033351 A1 | 2/2005 | Newton |
| 2005/0065589 A1 | 3/2005 | Schneider et al. |
| 2005/0125032 A1 | 6/2005 | Whisenant et al. |
| 2005/0137682 A1 | 6/2005 | Justino |
| 2005/0148925 A1* | 7/2005 | Rottenberg .......... A61B 5/0215 604/9 |
| 2005/0165344 A1 | 7/2005 | Dobak, III |
| 2005/0182486 A1 | 8/2005 | Gabbay |
| 2005/0267524 A1 | 12/2005 | Chanduszko |
| 2005/0283231 A1 | 12/2005 | Haug et al. |
| 2005/0288596 A1 | 12/2005 | Eigler et al. |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0025857 A1 | 2/2006 | Bergheim et al. |
| 2006/0052821 A1 | 3/2006 | Abbott et al. |
| 2006/0111660 A1 | 5/2006 | Wolf et al. |
| 2006/0111704 A1 | 5/2006 | Brenneman et al. |
| 2006/0116710 A1 | 6/2006 | Corcoran et al. |
| 2006/0122522 A1 | 6/2006 | Chavan et al. |
| 2006/0122647 A1 | 6/2006 | Callaghan et al. |
| 2006/0167541 A1 | 7/2006 | Lattouf |
| 2006/0184231 A1 | 8/2006 | Rucker |
| 2006/0212110 A1 | 9/2006 | Osborne et al. |
| 2006/0241745 A1 | 10/2006 | Solem |
| 2006/0256611 A1 | 11/2006 | Bednorz et al. |
| 2006/0282157 A1 | 12/2006 | Hill et al. |
| 2007/0010852 A1 | 1/2007 | Blaeser et al. |
| 2007/0021739 A1 | 1/2007 | Weber |
| 2007/0043435 A1 | 2/2007 | Seguin et al. |
| 2007/0073337 A1 | 3/2007 | Abbott et al. |
| 2007/0129756 A1 | 6/2007 | Abbott et al. |
| 2007/0191863 A1 | 8/2007 | De Juan et al. |
| 2007/0213813 A1 | 9/2007 | Von Segesser et al. |
| 2007/0249985 A1 | 10/2007 | Brenneman et al. |
| 2007/0276413 A1 | 11/2007 | Nobles |
| 2007/0276414 A1 | 11/2007 | Nobles |
| 2007/0282157 A1 | 12/2007 | Rottenberg et al. |
| 2007/0299384 A1 | 12/2007 | Faul et al. |
| 2008/0034836 A1 | 2/2008 | Eigler et al. |
| 2008/0086205 A1 | 4/2008 | Gordy et al. |
| 2008/0125861 A1 | 5/2008 | Webler et al. |
| 2008/0171944 A1 | 7/2008 | Brenneman et al. |
| 2008/0177300 A1 | 7/2008 | Mas et al. |
| 2008/0262602 A1 | 10/2008 | Wilk et al. |
| 2008/0319525 A1 | 12/2008 | Tieu et al. |
| 2009/0030499 A1 | 1/2009 | Bebb et al. |
| 2009/0054976 A1 | 2/2009 | Tuval et al. |
| 2009/0125104 A1 | 5/2009 | Hoffman |
| 2009/0149947 A1 | 6/2009 | Frohwitter |
| 2009/0198315 A1 | 8/2009 | Boudjemline |
| 2009/0276040 A1 | 11/2009 | Rowe et al. |
| 2009/0319037 A1 | 12/2009 | Rowe et al. |
| 2010/0004740 A1 | 1/2010 | Seguin et al. |
| 2010/0022940 A1 | 1/2010 | Thompson |
| 2010/0057192 A1 | 3/2010 | Celermajer |
| 2010/0069836 A1 | 3/2010 | Satake |
| 2010/0070022 A1 | 3/2010 | Kuehling |
| 2010/0081867 A1 | 4/2010 | Fishler et al. |
| 2010/0100167 A1 | 4/2010 | Bortlein et al. |
| 2010/0121434 A1 | 5/2010 | Paul et al. |
| 2010/0179590 A1 | 7/2010 | Fortson et al. |
| 2010/0191326 A1 | 7/2010 | Alkhatib |
| 2010/0249909 A1 | 9/2010 | McNamara et al. |
| 2010/0249910 A1 | 9/2010 | McNamara et al. |
| 2010/0249915 A1 | 9/2010 | Zhang |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324652 A1 | 12/2010 | Aurilia et al. |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1 | 4/2011 | Fischell et al. |
| 2011/0152923 A1 | 6/2011 | Fox |
| 2011/0190874 A1 | 8/2011 | Celermajer et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0257723 A1 | 10/2011 | McNamara |
| 2011/0264203 A1 | 10/2011 | Dwork et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0319806 A1 | 12/2011 | Wardle |
| 2012/0022507 A1 | 1/2012 | Najafi et al. |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | von Oepen et al. |
| 2012/0053686 A1 | 3/2012 | McNamara et al. |
| 2012/0071918 A1 | 3/2012 | Amin et al. |
| 2012/0130301 A1 | 5/2012 | McNamara et al. |
| 2012/0165928 A1 | 6/2012 | Nitzan et al. |
| 2012/0179172 A1 | 7/2012 | Paul et al. |
| 2012/0190991 A1 | 7/2012 | Bornzin et al. |
| 2012/0265296 A1 | 10/2012 | McNamara et al. |
| 2012/0271398 A1 | 10/2012 | Essinger et al. |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0046373 A1 | 2/2013 | Cartledge et al. |
| 2013/0096965 A1 | 4/2013 | Pappas et al. |
| 2013/0138145 A1 | 5/2013 | Von Oepen |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |
| 2013/0261531 A1 | 10/2013 | Gallagher et al. |
| 2013/0281988 A1 | 10/2013 | Magnin et al. |
| 2013/0304192 A1 | 11/2013 | Chanduszko |
| 2013/0331864 A1 | 12/2013 | Jelich et al. |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry et al. |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2015/0005810 A1 | 1/2015 | Center et al. |
| 2015/0034217 A1 | 2/2015 | Vad |
| 2015/0039084 A1 | 2/2015 | Levi et al. |
| 2015/0066140 A1 | 3/2015 | Quadri et al. |

(56) References Cited

U.S. PATENT DOCUMENTS

| | | |
|---|---|---|
| 2015/0073539 A1 | 3/2015 | Geiger et al. |
| 2015/0112383 A1 | 4/2015 | Sherman et al. |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | McNamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2015/0294313 A1 | 10/2015 | Kamal et al. |
| 2015/0313599 A1 | 11/2015 | Johnson et al. |
| 2015/0359556 A1 | 12/2015 | Vardi |
| 2016/0007924 A1 | 1/2016 | Eigler et al. |
| 2016/0022423 A1 | 1/2016 | McNamara et al. |
| 2016/0022970 A1 | 1/2016 | Forucci et al. |
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0157862 A1 | 6/2016 | Hernandez et al. |
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0035435 A1 | 2/2017 | Amin et al. |
| 2017/0056171 A1 | 3/2017 | Cooper et al. |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165532 A1 | 6/2017 | Khan et al. |
| 2017/0216025 A1 | 8/2017 | Nitzan et al. |
| 2017/0224323 A1 | 8/2017 | Rowe et al. |
| 2017/0224444 A1 | 8/2017 | Viecilli et al. |
| 2017/0231766 A1 | 8/2017 | Hariton et al. |
| 2017/0273790 A1 | 9/2017 | Vettukattil et al. |
| 2017/0281339 A1 | 10/2017 | Levi et al. |
| 2017/0312486 A1 | 11/2017 | Nitzan et al. |
| 2017/0319823 A1 | 11/2017 | Yacoby et al. |
| 2017/0325956 A1 | 11/2017 | Rottenberg et al. |
| 2017/0348100 A1 | 12/2017 | Lane et al. |
| 2018/0099128 A9 | 4/2018 | McNamara et al. |
| 2018/0104053 A1 | 4/2018 | Alkhatib et al. |
| 2018/0110609 A1 | 4/2018 | Ehnes et al. |
| 2018/0125630 A1 | 5/2018 | Hynes et al. |
| 2018/0130988 A1 | 5/2018 | Nishikawa et al. |
| 2018/0243071 A1* | 8/2018 | Eigler ................ A61F 2/01 |
| 2018/0256865 A1 | 9/2018 | Finch et al. |
| 2018/0263766 A1 | 9/2018 | Nitzan et al. |
| 2018/0344994 A1 | 12/2018 | Karavany et al. |
| 2019/0000327 A1 | 1/2019 | Doan et al. |
| 2019/0008628 A1 | 1/2019 | Eigler et al. |
| 2019/0015103 A1 | 1/2019 | Sharma |
| 2019/0015188 A1 | 1/2019 | Eigler et al. |
| 2019/0021861 A1 | 1/2019 | Finch |
| 2019/0239754 A1 | 8/2019 | Nabutovsky et al. |
| 2019/0336163 A1 | 11/2019 | McNamara et al. |
| 2020/0085600 A1 | 3/2020 | Schwartz et al. |
| 2020/0197178 A1 | 6/2020 | Vecchio |
| 2020/0261705 A1 | 8/2020 | Nitzan et al. |
| 2020/0315599 A1 | 10/2020 | Nae et al. |
| 2020/0368505 A1 | 11/2020 | Nae et al. |
| 2021/0052378 A1 | 2/2021 | Nitzan et al. |
| 2021/0100665 A1 | 4/2021 | Nae et al. |
| 2021/0121179 A1 | 4/2021 | Ben-David et al. |
| 2022/0008014 A1 | 1/2022 | Rowe et al. |
| 2022/0211361 A1 | 7/2022 | Rolando et al. |
| 2022/0304803 A1 | 9/2022 | Guyenot et al. |

FOREIGN PATENT DOCUMENTS

| | | | |
|---|---|---|---|
| EP | 1987777 A2 | 11/2008 | |
| EP | 2238933 A1 | 10/2010 | |
| EP | 2305321 A1 | 4/2011 | |
| EP | 1965842 B1 | 11/2011 | |
| EP | 3400907 A1 | 11/2018 | |
| FR | 2827153 A1 | 1/2003 | |
| WO | WO-9531945 A1 | 11/1995 | |
| WO | WO-9727898 A1 | 8/1997 | |
| WO | WO-99/60941 A1 | 12/1999 | |
| WO | WO-00/44311 A2 | 8/2000 | |
| WO | WO-0050100 A1 | 8/2000 | |
| WO | WO-0110314 A2 | 2/2001 | |
| WO | WO-0126585 A1 | 4/2001 | |
| WO | WO-0226281 A1 | 4/2002 | |
| WO | WO-02/071974 A2 | 9/2002 | |
| WO | WO-02087473 A1 | 11/2002 | |
| WO | WO-03/053495 A2 | 7/2003 | |
| WO | WO-2005/027752 A1 | 3/2005 | |
| WO | WO-2005/074367 A1 | 8/2005 | |
| WO | WO-2006/127765 A1 | 11/2006 | |
| WO | WO-2007/083288 A2 | 7/2007 | |
| WO | WO-2008/055301 A1 | 5/2008 | |
| WO | WO-2008070797 A2 | 6/2008 | |
| WO | WO-2009/029261 A1 | 3/2009 | |
| WO | WO-2010/128501 A1 | 11/2010 | |
| WO | WO-2010129089 A2 | 11/2010 | |
| WO | WO-2010/139771 A2 | 12/2010 | |
| WO | WO-2011/062858 A1 | 5/2011 | |
| WO | WO-2013/096965 A1 | 6/2013 | |
| WO | WO-2013096965 A1 * | 6/2013 | ......... A61B 17/0057 |
| WO | WO-2016/178171 A1 | 11/2016 | |
| WO | WO-2017/118920 A1 | 7/2017 | |
| WO | WO-2018158747 A1 | 9/2018 | |
| WO | WO-2019/015617 A1 | 1/2019 | |
| WO | WO-2019/085841 A1 | 5/2019 | |
| WO | WO-2019/109013 A1 | 6/2019 | |
| WO | WO-2019/142152 A1 | 7/2019 | |
| WO | WO-2019/179447 A1 | 9/2019 | |
| WO | WO-2019218072 A1 | 11/2019 | |
| WO | WO-2020206062 A1 | 10/2020 | |
| WO | WO-2020257530 A1 | 12/2020 | |
| WO | WO-2021050589 A1 | 3/2021 | |
| WO | WO-2021113670 A1 | 6/2021 | |
| WO | WO-2021212011 A2 | 10/2021 | |
| WO | WO-2021224736 A1 | 11/2021 | |
| WO | WO-2022046921 A1 | 3/2022 | |
| WO | WO-2022076601 A1 | 4/2022 | |
| WO | WO-2022091018 A1 | 5/2022 | |
| WO | WO-2022091019 A1 | 5/2022 | |
| WO | WO-2022103973 A1 | 5/2022 | |

OTHER PUBLICATIONS

U.S. Appl. No. 10/597,666, U.S. Pat. No. 8,070,708, filed Jun. 20, 2007, Dec. 6, 2011.

U.S. Appl. No. 12/223,080, U.S. Pat. No. 9,681,948, filed Jul. 16, 2014, Jun. 20, 2017.

U.S. Appl. No. 13/107,832, U.S. Pat. No. 8,235,933, filed May 13, 2011, Aug. 7, 2012.

U.S. Appl. No. 13/107,843, U.S. Pat. No. 8,328,751, filed May 13, 2011, Dec. 11, 2012.

U.S. Appl. No. 13/108,672, U.S. Pat. No. 9,724,499, filed May 16, 2011, Aug. 8, 2017.

U.S. Appl. No. 13/108,698, filed Jun. 16, 2011.

(56) References Cited

OTHER PUBLICATIONS

U.S. Appl. No. 13/108,850, filed May 16, 2011.
U.S. Appl. No. 13/108,880, U.S. Pat. No. 8,696,611, filed May 16, 2011, Apr. 15, 2014.
U.S. Appl. No. 13/193,309, U.S. Pat. No. 9,629,715, filed Jul. 28, 2011, Apr. 25, 2017.
U.S. Appl. No. 13/193,335, U.S. Pat. No. 9,034,034, filed Jul. 28, 2011, May 19, 2015.
U.S. Appl. No. 13/708,794, U.S. Pat. No. 9,943,670, filed Dec. 7, 2012, Apr. 17, 2018.
U.S. Appl. No. 14/154,080, U.S. Pat. No. 10,207,807, filed Jan. 13, 2014, Feb. 19, 2019.
U.S. Appl. No. 14/154,088, filed Jan. 13, 2014.
U.S. Appl. No. 14/154,093, filed Jan. 13, 2014.
U.S. Appl. No. 14/227,982, U.S. Pat. No. 9,707,382, filed Mar. 27, 2014, Jul. 18, 2017.
U.S. Appl. No. 14/282,615, U.S. Pat. No. 9,713,696, filed May 20, 2014, Jul. 25, 2017.
U.S. Appl. No. 14/712,801, U.S. Pat. No. 9,980,815, filed May 14, 2015, May 29, 2018.
U.S. Appl. No. 15/449,834, U.S. Pat. No. 10,076,403, filed Mar. 3, 2017, Sep. 18, 2018.
U.S. Appl. No. 15/492,852, U.S. Pat. No. 10,368,981, filed Apr. 20, 2017, Aug. 6, 2019.
U.S. Appl. No. 15/570,752, filed Oct. 31, 2017.
U.S. Appl. No. 15/608,948, filed May 30, 2017.
U.S. Appl. No. 15/624,314, U.S. Pat. No. 10,357,357, filed Jun. 15, 2017, Jul. 23, 2019.
U.S. Appl. No. 15/650,783, U.S. Pat. No. 10,639,459, filed Jul. 14, 2017, May 5, 2020.
U.S. Appl. No. 15/656,936, U.S. Pat. No. 10,478,594, filed Jul. 21, 2017, Nov. 19, 2019.
U.S. Appl. No. 15/668,622, U.S. Pat. No. 10,463,490, filed Aug. 3, 2017, Nov. 5, 2019.
U.S. Appl. No. 15/798,250, filed Oct. 30, 2017.
U.S. Appl. No. 15/988,888, filed May 24, 2018.
U.S. Appl. No. 16/130,978, U.S. Pat. No. 10,251,740, filed Sep. 13, 2018, Apr. 9, 2019.
U.S. Appl. No. 16/130,988, filed Sep. 13, 2018.
U.S. Appl. No. 16/205,213, filed Nov. 29, 2018.
U.S. Appl. No. 16/374,698, filed Apr. 3, 2019.
U.S. Appl. No. 16/395,209, filed Apr. 25, 2019.
U.S. Appl. No. 16/408,419, filed May 9, 2019.
U.S. Appl. No. 16/505,624, filed Jul. 8, 2019.
U.S. Appl. No. 16/672,420, filed Nov. 1, 2019.
U.S. Appl. No. 16/686,013, filed Nov. 15, 2019.
U.S. Appl. No. 16/866,377, filed May 4, 2020.
U.S. Appl. No. 16/875,652, filed May 15, 2020.
Ando et al., "Left ventricular decompression through a patent foramen ovale in a patient with hypertropic cardiomyopathy: A case report," Cardiovascular Ultrasound 2: 1-7 (2004).
Atrium Advanta V12, Balloon Expandable Covered Stent, Improving Patient Outcomes with An Endovascular Approach, Brochure-8 pages, Getinge (2017).
Boehm, et al., Balloon Atrial Septostomy: History and Technique, Images Paeditr. Cardiol., 8(1):8-14 (2006).
Braunwald, Heart Disease, Chapter 6, p. 186.
Bridges, et al., The Society of Thoracic Surgeons Practice Guideline Series: Transmyocardial Laser Revascularization, Ann Thorac Surg., 77:1494-1502 (2004).
Bristow et al., Improvement in cardiac myocite function by biological effects of medical therapy: a new concept in the treatment of heart failure, European Heart Journal 16 (Suppl.F): 20-31 (1995).
Case et al., "Relief of High Left-Atrial Pressure in Left-Ventricular Failure," Lancet, pp. 841-842 (Oct. 14, 1964).
Coats et al., "Controlled trial of physical training in chronic heart failure: Exercise performance, hemodynamics, ventilation and autonomic function," Circulation 85:2119-2131 (1992).
Davies et al., "Reduced contraction and altered frequency response of isolated ventricular myocytes from patients with heart failure," Circulation 92: 2540-2549 (1995).
Drexel, et al., The Effects of Cold Work and Heat Treatment on the Properties of Nitinol Wire, Proceedings of the International Conference on Shape Memory and Superelastic Technologies, May 7-11, 2006, Pacific Grove, California, USA (pp. 447-454).
Eigler, et al., Implantation and Recovery of Temporary Metallic Stents in Canine Coronary Arteries, JACC, 22(4):1207-1213 (1993).
Ennezat et al., An unusual case of low-flow, low-gradient severe aortic stenosis: Left-to-right shunt due to atrial septal defect, Cardiology 113(2): 146-148 (2009).
Ewert et al., "Acute left heart failure after interventional occlusion of an atrial septal defect," Z Kardiol. 90(5): 362-366 (May 2001).
Ewert et al., Masked Left Ventricular Restriction in Elderly Patients With Atrial Septal Defects: A Contraindication for Closure?, Catheterization and Cardiovascular Interventions 52: 177-180 (2001).
Extended EP Search Report dated Sep. 19, 2016 in EP Patent Application Serial No. 16170281.6.
Extended European Search Report dated Jan. 8, 2015 in EP Patent Appl. No. 10772089.8.
Geiran et al., "Changes in cardiac dynamics by opening an interventricular shunt in dogs," J. Surg. Res. 48(1): 6-12 (Jan. 1990).
Gelernter-Yaniv et al., "Transcatheter closure of left-to-right interatrial shunts to resolve hypoxemia," Conginit. Heart Dis. 31(1) 47-53 (Jan. 2008).
Gewillig et al., "Creation with a stent of an unrestrictive lasting atrial communication," Cardio. Young 12(4): 404-407 (2002).
International Search Report & Written Opinion dated May 29, 2018 in Int'l PCT Patent Appl. Serial No. PCTIB2018/051355.
International Search Report for PCT/IL2005/000131, 3 pages (dated Apr. 7, 2008).
International Search Report for PCT/IL2010/000354 dated Aug. 25, 2010 (1 pg).
Int'l Search Report & Written Opinion dated Feb. 16, 2015 in Int'l PCT Patent Appl. Serial No. PCT/IB2014/001771.
International Search Report & Written Opinion dated Feb. 7, 2020 in Int'l PCT Patent Appl. Serial No. PCT/IB2019/060257.
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer et al., "Controlled study of captopril in chronic heart failure: A rest and exercise hemodynamic study," Circulation 67(4): 807-816 (1983).
Lai et al., Bidirectional Shunt Through a Residual Atrial Septal Defect After Percutaneous Transvenous Mitral Commissurotomy, Cardiology 83(3): 205-207 (1993).
Lemmer et al., "Surgical implications of atrial septal defect complicating aortic balloon valvuloplasty," Ann Thorac. Surg. 48(2): 295-297 (Aug. 1989).
Merriam-Webster "Definition of 'Chamber'," O-line Dictionary 2004, Abstract.
Park, et al., Blade Atrial Septostomy: Collaborative Study, Circulation, 66(2):258-266 (1982).
Partial International Search dated Aug. 17, 2017 in Int'l PCT Patent Appl. Serial No. PCT/IB2017/053188.
Partial Supplemental European Search Report dated Dec. 11, 2018 in EP Patent Appl. Serial No. 1678939.6 (1830).
Roven et al., "Effect of Compromising Right Ventricular Function in Left Ventricular Failure by Means of Interatrial and Other Shunts," American Journal Cardiology, 24:209-219 (1969).
Salehian et al., Improvements in Cardiac Form and Function After Transcatheter Closure of Secundum Atrial Septal Defects, Journal of the American College of Cardiology, 45(4):499-504 (2005).
Schmitto et al., Chronic heart failure induced by multiple sequential coronary microembolization in sheep, The International Journal of Artificial Organs, 31(4):348-353 (2008).
Schubert et al., Left Ventricular Conditioning in the Elderly Patient to Prevent Congestive Heart Failure After Transcatheter Closure of the Atrial Septal Defect, Catheterization and Cardiovascular Interventions, 64(3): 333-337 (2005).
Stormer et al., Comparative Study of n vitro Flow Characteristics Between a Human Aortic Valve and a Designed Aortic Valve and

(56) References Cited

OTHER PUBLICATIONS

Six Corresponding Types of Prosthetic Heart Valves, European Surgical Research 8(2): 117-131 (1976).
Stumper et al., "Modified technique of stent fenestration of the atrial septum," Heart 89: 1227-1230 (2003).
Trainor et al., Comparative Pathology of an Implantable Left Atrial Pressure Sensor, ASAIO Journal, Clinical Cardiovascular/Cardiopulmonary Bypass, 59(5):486-92 (2013).
Zhou et al., Unidirectional Valve Patch for Repair of Cardiac Septal Defects With Pulmonary Hypertension, Annals of Thoracic Surgeons, 60:1245-1249 (1995).
Abraham et al., "Hemodynamic Monitoring in Advanced Heart Failure: Results from the LAPTOP-HF Trial," J Card Failure, 22:940 (2016) (Abstract Only).
Abraham et al., "Sustained efficacy of pulmonary artery pressure to guide adjustment of chronic heart failure therapy: complete follow-up results from the CHAMPION randomised trial," The Lancet, doi.org/10.1016/S0140-6736(15)00723-0 (2015).
Abraham et al., "Wireless pulmonary artery haemodynamic monitoring in chronic heart failure: a randomised controlled trial," The Lancet, DOI:10.1016/S0140-6736(11)60101-3 (2011).
Abreu et al., "Doppler ultrasonography of the femoropopliteal segment in patients with venous ulcer," J Vasc Bras., 11(4):277-285 (2012).
Adamson et al., "Ongoing Right Ventricular Hemodynamics in Heart Failure Clinical Value of Measurements Derived From an Implantable Monitoring System," J Am Coll Cardiol., 41(4):565-571 (2003).
Adamson et al., "Wireless Pulmonary Artery Pressure Monitoring Guides Management to Reduce Decompensation in Heart Failure With Preserved Ejection Fraction," Circ Heart Fail., 7:935-944 (2014).
Ambrosy et al. "The Global Health and Economic Burden of Hospitalizations for Heart Failure," J Am Coll Cardiol., 63:1123-1133 (2014).
Aminde et al., "Current diagnostic and treatment strategies for Lutembacher syndrome: the pivotal role of echocardiography," Cardiovasc Diagn Ther., 5(2):122-132 (2015).
Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).
Anderas et al., "Tilted c-axis Thin-Film Bulk Wave Resonant Pressure Sensors with Improved Sensitivity," IEEE Sensors J., 12(8):2653-2654 (2012).
Article 34 Amendments dated May 28, 2013 in Int'l PCT Patent Appl. Serial No. PCT/IB2012/001859 (0810).
Article 34 Amendments dated Nov. 27, 2012 in Int'l PCT Patent Appl. Serial No. PCT/IL2011/000958 (0710).
Ataya et al., "A Review of Targeted Pulmonary Arterial Hypertension-Specific Pharmacotherapy," J. Clin. Med., 5(12):114 (2016).
Bannan et al., "Characteristics of Adult Patients with Atrial Septal Defects Presenting with Paradoxical Embolism.," Catheterization and Cardiovascular Interventions, 74:1066-1069 (2009).
Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).
Beemath et al., "Pulmonary Embolism as a Cause of Death in Adults Who Died With Heart Failure," Am J Cardiol., 98:1073-1075 (2006).
Benza et al., "Monitoring Pulmonary Arterial Hypertension Using an Implantable Hemodynamic Sensor," CHEST, 156(6):1176-1186 (2019).
Borlaug, et al., Latent Pulmonary Vascular Disease May Alter The Response to Therapeutic Atrial Shunt Device in Heart Failure, Circulation (Mar. 2022).
Bruch et al., "Fenestrated Occluders for Treatment of ASD in Elderly Patients with Pulmonary Hypertension and/or Right Heart Failure," J Interven Cardiol., 21(1):44-49 (2008).
Burkhoff et al., "Assessment of systolic and diastolic ventricular properties via pressure-volume analysis: a guide for clinical, translational, and basic researchers," Am J Physiol Heart Circ Physiol., 289:H501-H512 (2005).
Butler et al. "Recognizing Worsening Chronic Heart Failure as an Entity and an End Point in Clinical Trials," JAMA., 312(8):789-790 (2014).
Chakko et al., "Clinical, radiographic, and hemodynamic correlations in chronic congestive heart failure: conflicting results may lead to inappropriate care," Am J Medicine, 90:353-359 (1991) (Abstract Only).
Chang et al., "State-of-the-art and recent developments in micro/nanoscale pressure sensors for smart wearable devices and health monitoring systems," Nanotechnology and Precision Engineering, 3:43-52 (2020).
Chen et al., "Continuous wireless pressure monitoring and mapping with ultra-small passive sensors for health monitoring and critical care," Nature Communications, 5(1):1-10 (2014).
Chen et al., "National and Regional Trends in Heart Failure Hospitalization and Mortality Rates for Medicare Beneficiaries, 1998-2008," JAMA, 306(15):1669-1678 (2011).
Chiche et al., "Prevalence of patent foramen ovale and stroke in pulmonary embolism patients," Eur Heart J., 34:P1142 (2013) (Abstract Only).
Chin et al., "The right ventricle in pulmonary hypertension," Coron Artery Dis., 16(1):13-18 (2005) (Abstract Only).
Chun et al., "Lifetime Analysis of Hospitalizations and Survival of Patients Newly Admitted With Heart Failure," Circ Heart Fail., 5:414-421 (2012).
Ciarka et al., "Atrial Septostomy Decreases Sympathetic Overactivity in Pulmonary Arterial Hypertension," Chest, 131(6):P1831-1837 (2007) (Abstract Only).
Cleland et al., "The EuroHeart Failure survey programme-a survey on the quality of care among patients with heart failure in Europe—Part 1: patient characteristics and diagnosis," Eur Heart J., 24:442-463 (2003).
Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).
Clowes, et al., Mechanisms of Arterial Graft Healing—Rapid Transmural Capillary Ingrowth Provides a Source of Intimal Endothelium and Smooth Muscle in Porous PTFE Prostheses, Am. J. Pathol., 123(2):220-230 (May 1986).
Davies et al., "Abnormal left heart function after operation for atrial septal defect," British Heart Journal, 32:747-753 (1970).
Del Trigo et al., "Unidirectional Left-To-Right Interatrial Shunting for Treatment of Patients with Heart Failure with Reduced Ejection Fraction: a Safety and Proof-of-Principle Cohort Study," Lancet, 387:1290-1297 (2016).
Della Lucia et al., "Design, fabrication and characterization of SAW pressure sensors for offshore oil and gas exploration," Sensors and Actuators A: Physical, 222:322-328 (2015).
Drazner et al., "Prognostic Importance of Elevated Jugular Venous Pressure and a Third Heart Sound in Patients with Heart Failure," N Engl J Med., 345(8):574-81 (2001).
Drazner et al., "Relationship between Right and Left-Sided Filling Pressures in 1000 Patients with Advanced Heart Failure," Heart Lung Transplant, 18:1126-1132 (1999).
Eigler et al., "Cardiac Unloading with an Implantable Interatrial Shunt in Heart Failure: Serial Observations in an Ovine Model of Ischemic Cardiomyopathy," Structural Heart, 1:40-48 (2017).
Eshaghian et al., "Relation of Loop Diuretic Dose to Mortality in Advanced Heart Failure," Am J Cardiol., 97:1759-1764 (2006).
Extended European Search Report dated Mar. 29, 2019 in EP Patent Appl. Serial No. EP16789391 (1830).
Feldman et al., "Transcatheter Interatrial Shunt Device for the Treatment of Heart Failure with Preserved Ejection Fraction (Reduce

(56) References Cited

OTHER PUBLICATIONS

Lap-HF I [Reduce Elevated Left Atrial Pressure in Patients With Heart Failure]), A Phase 2, Randomized, Sham-Controlled Trial," Circulation, 137:364-375 (2018).
Ferrari et al., "Impact of pulmonary arterial hypertension (PAH) on the lives of patients and carers: results from an international survey," Eur Respir J., 42:26312 (2013) (Abstract Only).
Flachskampf, et al., Influence of Orifice Geometry and Flow Rate on Effective Valve Area: An In Vitro Study, Journal of the American College of Cardiology, 15(5):1173-1180 (Apr. 1990).
Fonarow et al., "Characteristics, Treatments, and Outcomes of Patients With Preserved Systolic Function Hospitalized for Heart Failure," J Am Coll Cardiol., 50(8):768-777 (2007).
Fonarow et al., "Risk Stratification for In-Hospital Mortality in Acutely Decompensated Heart Failure: Classification and Regression Tree Analysis," JAMA, 293(5):572-580 (2005).
Fonarow, G., "The Treatment Targets in Acute Decompensated Heart Failure," Rev Cardiovasc Med., 2:(2):S7-S12 (2001).
Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).
Galie et al., "Pulmonary arterial hypertension: from the kingdom of the near-dead to multiple clinical trial meta-analyses," Eur Heart J., 31:2080-2086 (2010).
Galipeau et al., "Surface acoustic wave microsensors and applications," Smart Materials and Structures, 6(6):658-667 (1997) (Abstract Only).
Geva et al., "Atrial septal defects," Lancet, 383:1921-32 (2014).
Gheorghiade et al., "Acute Heart Failure Syndromes, Current State and Framework for Future Research," Circulation, 112:3958-3968 (2005).
Gheorghiade et al., "Effects of Tolvaptan, a Vasopressin Antagonist, in Patients Hospitalized With Worsening Heart Failure A Randomized Controlled Trial," JAMA., 291:1963-1971 (2004).
Go et al. "Heart Disease and Stroke Statistics—2014 Update—A Report From the American Heart Association," Circulation, 128:1-267 (2014).
Greitz, et al., Pulsatile Brain Movement and Associated Hydrodynamics Studied by Magnetic Resonance Phase Imaging, Diagnostic Neuroradiology, 34(5): 370-380 (1992).
Guillevin et al., "Understanding the impact of pulmonary arterial hypertension on patients'and carers' lives," Eur Respir Rev., 22:535-542 (2013).
Guyton et al., "Effect of Elevated Left Atrial Pressure and Decreased Plasma Protein Concentration on the Development of Pulmonary Edema," Circulation Research, 7:643-657 (1959).
Hasenfub, et al., A Transcatheter Intracardiac Shunt Device for Heart Failure with Preserved Ejection Fraction (Reduce Lap-HF): A Multicentre, Open-Label, Single-Arm, Phase 1 Trial, www.thelancet.com, 387:1298-1304 (2016).
Hoeper et al., "Definitions and Diagnosis of Pulmonary Hypertension," J Am Coll Cardiol., 62(5):D42-D50 (2013).
Hogg et al., "Heart Failure With Preserved Left Ventricular Systolic Function. Epidemiology, Clinical Characteristics, and Prognosis," J Am Coll Cardiol., 43(3):317-327 (2004).
Howell et al., "Congestive heart failure and outpatient risk of venous thromboembolism: A retrospective, case-control study," Journal of Clinical Epidemiology, 54:810-816 (2001).
Huang et al., "Remodeling of the chronic severely failing ischemic sheep heart after coronary microembolization: functional, energetic, structural, and cellular responses," Am J Physiol Heart Circ Physiol., 286:H2141-H2150 (2004).
Humbert et al., "Pulmonary Arterial Hypertension in France—Results from a National Registry," Am J Respir Crit Care Med., 173:1023-1030 (2006).
International Search Report & Written Opinion dated Nov. 7, 2016 in Int'l PCT Patent Appl. Serial No. PCT/IB2016/052561 (1810).
International Search Report & Written Opinion dated May 29, 2018 in Int'l PCT Patent Appl. Serial No. PCT/IB2018/051385 (1310).
International Search Report & Written Opinion dated Feb. 3, 2023 in Int'l PCT Patent Appl. Serial No. PCT/IB2022/060621 (2210).
International Search Report & Written Opinion dated Feb. 6, 2013 in Int'l PCT Patent Appl. No. PCT/IB2012/001859, 12 pages (0810).
International Search Report & Written Opinion dated Feb. 9, 2022 in Int'l PCT Patent Appl. Serial No. PCT/IB2021/060473 (2010).
International Search Report & Written Opinion dated Mar. 29, 2023 in Int'l PCT Patent Appl. Serial No. PCT/IB2023/050743 (2410).
International Search Report & Written Opinion dated May 13, 2019 in Int'l PCT Patent Appl. No. PCT/IB2019/050452 (1610).
International Search Report & Written Opinion dated May 17, 2022 in Int'l PCT Patent Appl. Serial No. PCT/IB2022/051177 (2310).
International Search Report & Written Opinion dated Jul. 14, 2020 in Int'l PCT Patent Appl. Serial No. PCT/IB2020/053832 (1210).
International Search Report & Written Opinion dated Jul. 20, 2020 in Int'l PCT Patent Appl. Serial No. PCT/IB2020/054699 (1710).
International Search Report & Written Opinion dated Jul. 23, 2021 in Int'l PCT Patent Appl. Serial No. PCT/IB2021/053594 (1910).
International Search Report & Written Opinion dated Aug. 12, 2020 in Int'l PCT Patent Appl. Serial No. PCT/IB2020/053118 (1010).
International Search Report & Written Opinion dated Aug. 28, 2012 in Int'l PCT Patent Appl. No. PCT/IL2011/000958 (0710).
International Search Report & Written Opinion dated Sep. 21, 2020 in Int'l PCT Patent Appl. Serial No. PCT/IB2020/054306 (1510).
International Search Report & Written Opinion dated Oct. 26, 2007 in Int'l PCT Patent Appl. Serial No. PCT/IB07/50234 (0610).
Jessup et al. "2009Focused Update: ACC/AHA Guidelines for the Diagnosis and Management of Heart Failure in Adults: A Report of the American College of Cardiology Foundation/American Heart Association Task Force on Practice Guidelines: Developed in Collaboration With the International Society for Heart and Lung Transplantation," J. Am. Coll. Cardiol., 53:1343-1382 (2009).
Jiang, G., "Design challenges of implantable pressure monitoring system," Frontiers in Neuroscience, 4(29):1-4 (2010).
Kane et al., "Integration of clinical and hemodynamic parameters in the prediction of long-term survival in patients with pulmonary arterial hypertension," Chest, 139(6):1285-1293 (2011) (Abstract Only).
Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).
Kaye, et al., One-Year Outcomes After Transcatheter Insertion of an Interatrial Shunt Device for the Management of Heart Failure with Preserved Ejection Fraction, Circulation: Heart Failure, 9(12):e003662 (Dec. 2016).
Keogh et al., "Interventional and Surgical Modalities of Treatment in Pulmonary Hypertension," J Am Coll Cardiol., 54:S67-77 (2009).
Keren, et al. Methods and Apparatus for Reducing Localized Circulatory System Pressure,., Jan. 7, 2002 (pp. 16).
Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
Lammers et al., "Efficacy and Long-Term Patency of Fenerstrated Amplatzer Devices in Children," Catheter Cardiovasc Interv., 70:578-584 (2007).

(56) References Cited

OTHER PUBLICATIONS

Lindenfeld et al. "Executive Summary: HFSA 2010 Comprehensive Heart Failure Practice Guideline," J. Cardiac Failure, 16(6):475-539 (2010).

Luo, Yi, *Selective and Regulated RF Heating of Stent Toward Endohyperthermia Treatment of In-Stent Restenosis*, A Thesis Submitted in Partial Fulfillment of The Requirements For The Degree of Master of Applied Science in The Faculty of Graduate and Postdoctoral Studies (Electrical and Computer Engineering), The University of British Columbia, Vancouver, Dec. 2014.

MacDonald et al., "Emboli Enter Penetrating Arteries of Monkey Brain in Relation to Their Size," Stroke, 26:1247-1251 (1995).

Maluli et al., "Atrial Septostomy: A Contemporary Review," Clin. Cardiol., 38(6):395-400 (2015).

Maurer et al., "Rationale and Design of the Left Atrial Pressure Monitoring to Optimize Heart Failure Therapy Study (LAPTOP-HF)," Journal of Cardiac Failure., 21(6): 479-488 (2015).

McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).

McLaughlin et al., "Management of Pulmonary Arterial Hypertension," J Am Coll Cardiol., 65(18):1976-1997 (2015).

McLaughlin et al., "Survival in Primary Pulmonary Hypertension—The Impact of Epoprostenol Therapy.," Circulation, 106:1477-1482 (2002).

Mu et al., "Dual mode acoustic wave sensor for precise pressure reading," Applied Physics Letters, 105:113507-1-113507-5 (2014).

Nagaraju et al., "A 400μW Differential FBAR Sensor Interface IC with digital readout," IEEE., pp. 218-221 (2015).

Noordegraaf et al., "The role of the right ventricle in pulmonary arterial hypertension," Eur Respir Rev., 20(122):243-253 (2011).

O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).

Oktay et al., "The Emerging Epidemic of Heart Failure with Preserved Ejection Fraction," Curr Heart Fail Rep., 10(4):1-17 (2013).

Owan et al., "Trends in Prevalence and Outcome of Heart Failure with Preserved Ejection Fraction," N Engl J Med., 355:251-259 (2006).

Paitazoglou et al., "Title: The AFR-Prelieve Trial: A prospective, non-randomized, pilot study to assess the Atrial Flow Regulator (AFR) in Heart Failure Patients with either preserved or reduced ejection fraction," EuroIntervention, 28:2539-50 (2019).

Park Blade Septostomy Catheter Instructions for Use, Cook Medical, 28 pages, Oct. 2015.

Peters et al., "Self-fabricated fenestrated Amplatzer occluders for transcatheter closure of atrial septal defect in patients with left ventricular restriction: midterm results," Clin Res Cardiol., 95:88-92 (2006).

Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi:10.1093/eurheartj/ehw128 (2016).

Potkay, J. A., "Long term, implantable blood pressure monitoring systems," Biomed Microdevices, 10:379-392 (2008).

Pretorious et al., "An Implantable Left Atrial Pressure Sensor Lead Designed for Percutaneous Extraction Using Standard Techniques," PACE, 00:1-8 (2013).

Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).

Rich et al., "Atrial Septostomy as Palliative Therapy for Refractory Primary Pulmonary Hypertension," Am J Cardiol., 51:1560-1561 (1983).

Ritzema et al., "Direct Left Atrial Pressure Monitoring in Ambulatory Heart Failure Patients—Initial Experience With a New Permanent Implantable Device," Circulation, 116:2952-2959 (2007).

Ritzema et al., "Physician-Directed Patient Self-Management of Left Atrial Pressure in Advanced Chronic Heart Failure," Circulation, 121:1086-1095 (2010).

Roberts et al., "Integrated microscopy techniques for comprehensive pathology evaluation of an implantable left atrial pressure sensor," J Histotechnology, 36(1):17-24 (2013).

Rodes-Cabau et al., "Interatrial Shunting for Heart Failure Early and Late Results From the First-in-Human Experience With the V-Wave System," J Am Coll Cardiol Intv., 11:2300- 2310.doi:10.1016/j.cin.2018.07.001 (2018).

Rosenquist et al., Atrial Septal Thickness and Area in Normal Heart Specimens and in Those With Ostium Secundum Atrial Septal Defects, J. Clin. Ultrasound, 7:345-348 (1979).

Ross et al., "Interatrial Communication and Left Atrial Hypertension—A Cause of Continuous Murmur," Circulation, 28:853-860 (1963).

Rossignol, et al., Left-to-Right Atrial Shunting: New Hope for Heart Failure, www.thelancet.com, 387:1253-1255 (2016).

Sandoval et al., "Effect of atrial septostomy on the survival of patients with severe pulmonary arterial hypertension," Eur Respir J., 38:1343-1348 (2011).

Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).

Schiff et al., "Decompensated heart failure: symptoms, patterns of onset, and contributing factors," Am J. Med., 114(8):625-630 (2003) (Abstract Only).

Schneider et al., "Fate of a Modified Fenestration of Atrial Septal Occluder Device after Transcatheter Closure of Atrial Septal Defects in Elderly Patients," J Interven Cardiol., 24:485-490 (2011).

Scholl et al., "Surface Acoustic Wave Devices for Sensor Applications," Phys Status Solidi Appl Res., 185(1):47-58 (2001) (Abstract Only).

Setoguchi et al., "Repeated hospitalizations predict mortality in the community population with heart failure," Am Heart J., 154:260-266 (2007).

Shah, et al., Atrial Shunt Device For Heart Failure With Preserved And Mildly Reduced Ejection Fraction (Reduce Lap-HF II): A Randomised, Multicentre, Blinded, Sham-Controlled Trial, The Lancet, 399(10330):1130-1140 (Mar. 2022).

Shah et al., "Heart Failure With Preserved, Borderline, and Reduced Ejection Fraction—5-Year Outcomes," J Am Coll Cardiol., https://doi.org/10.1016/j.jacc.2017.08.074 (2017).

Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (Reduce Lap-HF I) Trial—A Randomized Clinical Trial," JAMA Cardiol. doi:10.1001/jamacardio.2018.2936 (2018).

Sitbon et al., "Selexipag for the Treatment of Pulmonary Arterial Hypertension.," N Engl J Med., 373(26):2522-2533 (2015).

Sitbon et al., "Epoprostenol and pulmonary arterial hypertension: 20 years of clinical experience," Eur Respir Rev., 26:160055:1-14 (2017).

Steimle et al., "Sustained Hemodynamic Efficacy of Therapy Tailored to Reduce Filling Pressures in Survivors With Advanced Heart Failure," Circulation, 96:1165-1172 (1997).

Stevenson et al., "The Limited Reliability of Physical Signs for Estimating Hemodynamics in Chronic Heart Failure," JAMA, 261(6):884-888 (1989) (Abstract Only).

Su et al., "A film bulk acoustic resonator pressure sensor based on lateral field excitation," International Journal of Distributed Sensor Networks, 14(11):1-8 (2018).

Supplementary European Search Report dated Nov. 13, 2009 in EP Patent Appl. Serial No. 05703174.2 (0430).

Thenappan et al., "Evolving Epidemiology of Pulmonary Arterial Hypertension," Am J Resp Critical Care Med., 186:707-709 (2012).

Tomai et al., "Acute Left Ventricular Failure After Transcatheter Closure of a Secundum Atrial Septal Defect in a Patient With

(56) References Cited

OTHER PUBLICATIONS

Coronary Artery Disease: A Critical Reappraisal," Catheterization and Cardiovascular Interventions, 55:97-99 (2002).

Torbicki et al., "Atrial Septostomy," The Right Heart, 305-316 (2014).

Troost et al., "A Modified Technique of Stent Fenestration of the Interatrial Septum Improves Patients With Pulmonary Hypertension," Catheterization and Cardiovascular Interventions, 73:173179 (2009).

Troughton et al., "Direct Left Atrial Pressure Monitoring in Severe Heart Failure: Long-Term Sensor Performance," J. of Cardiovasc. Trans. Res., 4:3-13 (2011).

Vank-Noordegraaf et al., "Right Heart Adaptation to Pulmonary Arterial Hypertension—Physiology and Pathobiology," J Am Coll Cardiol., 62(25):D22-33 (2013).

Verel et al., "Comparison of left atrial pressure and wedge pulmonary capillary pressure—Pressure gradients between left atrium and left ventricle," British Heart J., 32:99-102 (1970).

Viaene et al., "Pulmonary oedema after percutaneous ASD-closure," Acta Cardiol., 65(2):257-260 (2010).

Wang et al., "A Low Temperature Drifting Acoustic Wave Pressure Sensor with an Integrated Vacuum Cavity for Absolute Pressure Sensing," Sensors, 20(1788):1-13 (2020).

Wang et al., "Tire Pressure Monitoring System and Wireless Passive Surface Acoustic Wave Sensor," Appl Mech Mater., 536(537):333-337 (2014).

Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).

Webb et al., "Atrial Septal Defects in the Adult Recent Progress and Overview," Circulation, 114:1645-1653 (2006).

Wiedemann, H.R., "Earliest description by Johann Friedrich Meckel, Senior (1750) of what is known today as Lutembacher syndrome (1916)," Am J Med Genet., 53(1):59-64 (1994) (Abstract Only).

Written Opinion of the International Searching Authority dated Apr. 7, 2008 in Int'l PCT Patent Appl. Serial No. PCT/IL05/00131 (0410).

Yantchev et al., "Thin Film Lamb Wave Resonators in Frequency Control and Sensing Applications: A Review," Journal of Micromechanics and Microengineering, 23(4):043001 (2013).

Zhang et al., "Acute left ventricular failure after transcatheter closure of a secundum atrial septal defect in a patient with hypertrophic cardiomyopathy," Chin Med J., 124(4):618-621 (2011).

Zhang et al., "Film bulk acoustic resonator-based high-performance pressure sensor integrated with temperature control system," J Micromech Microeng., 27(4):1-10 (2017).

* cited by examiner

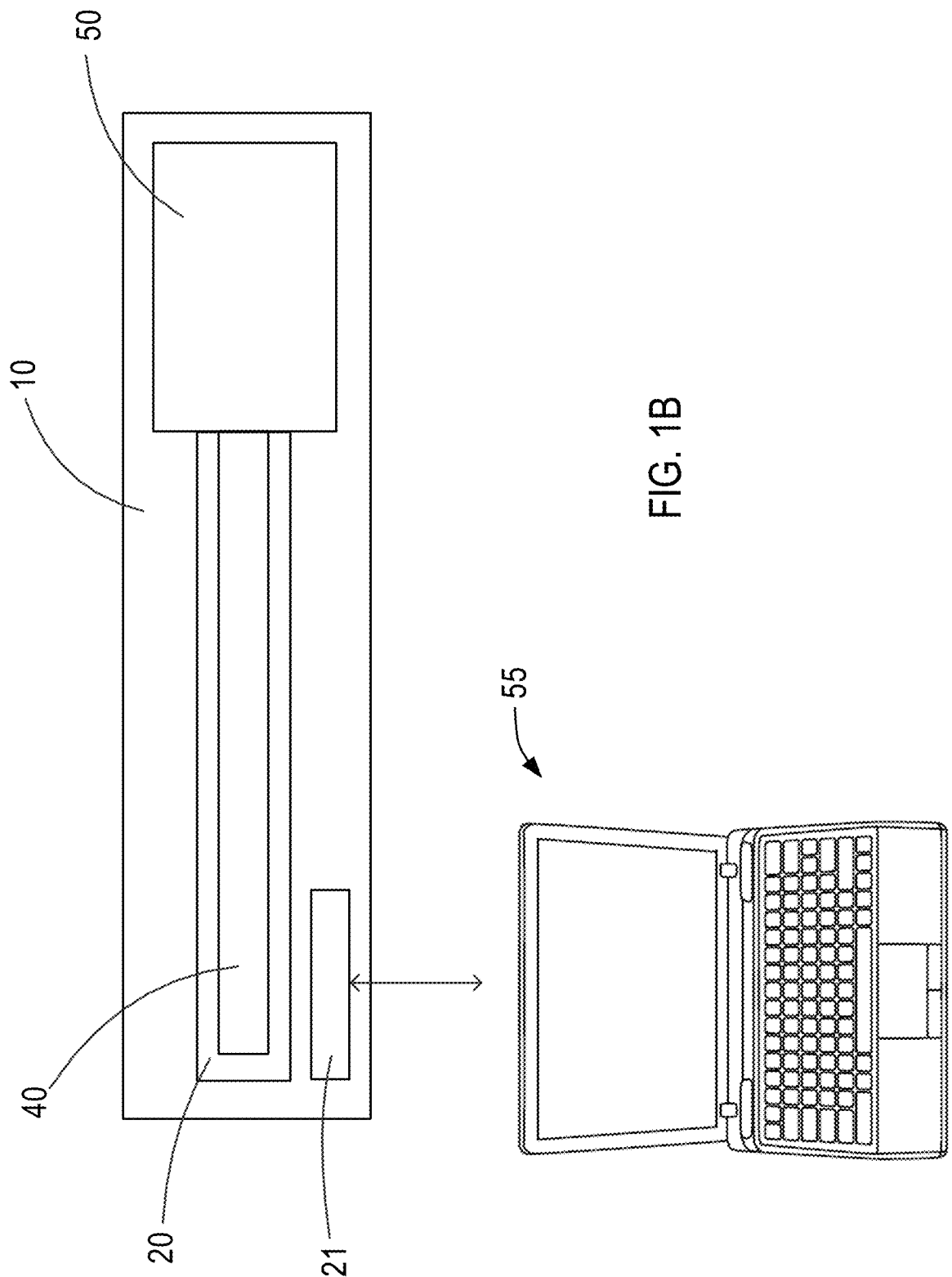

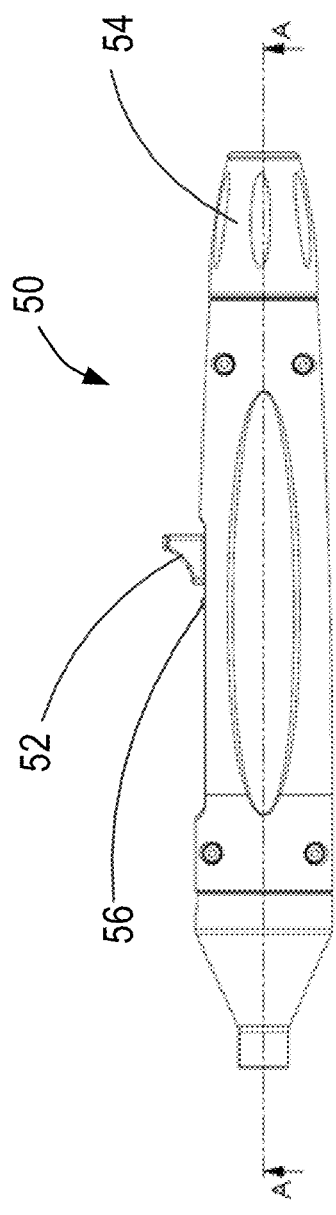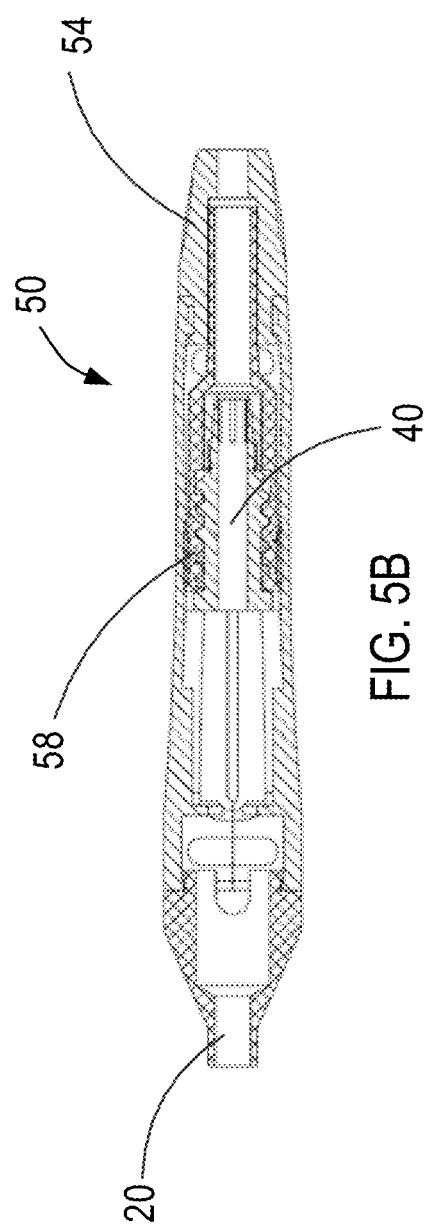
FIG. 5A
FIG. 5B

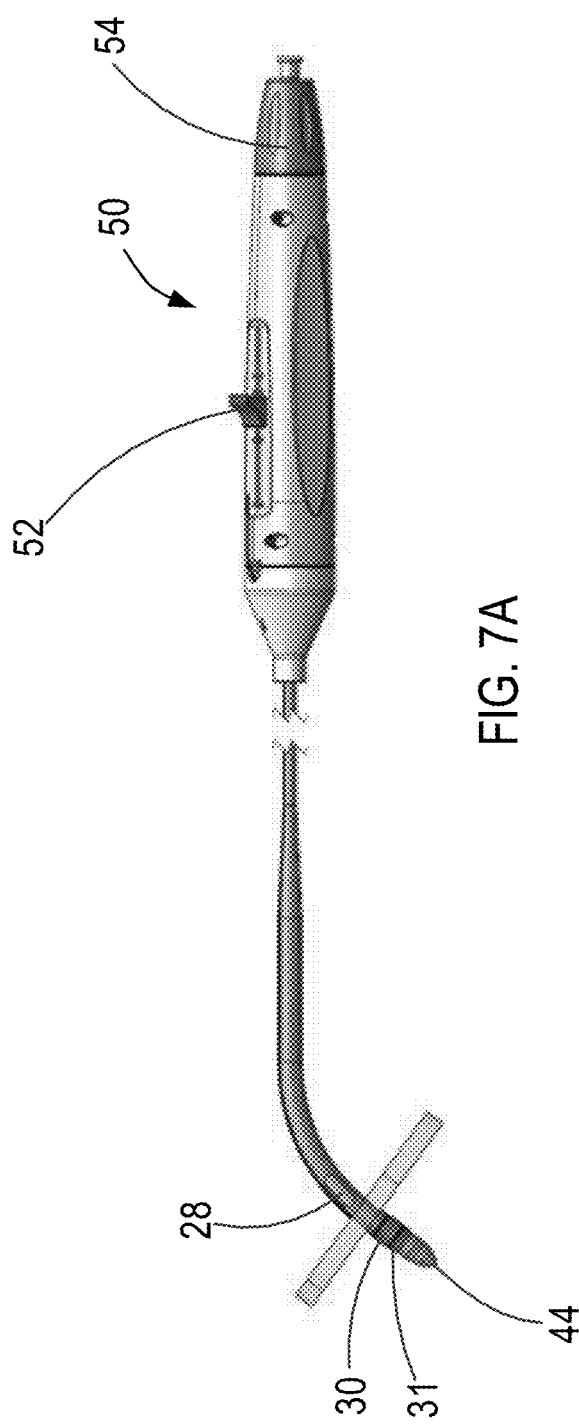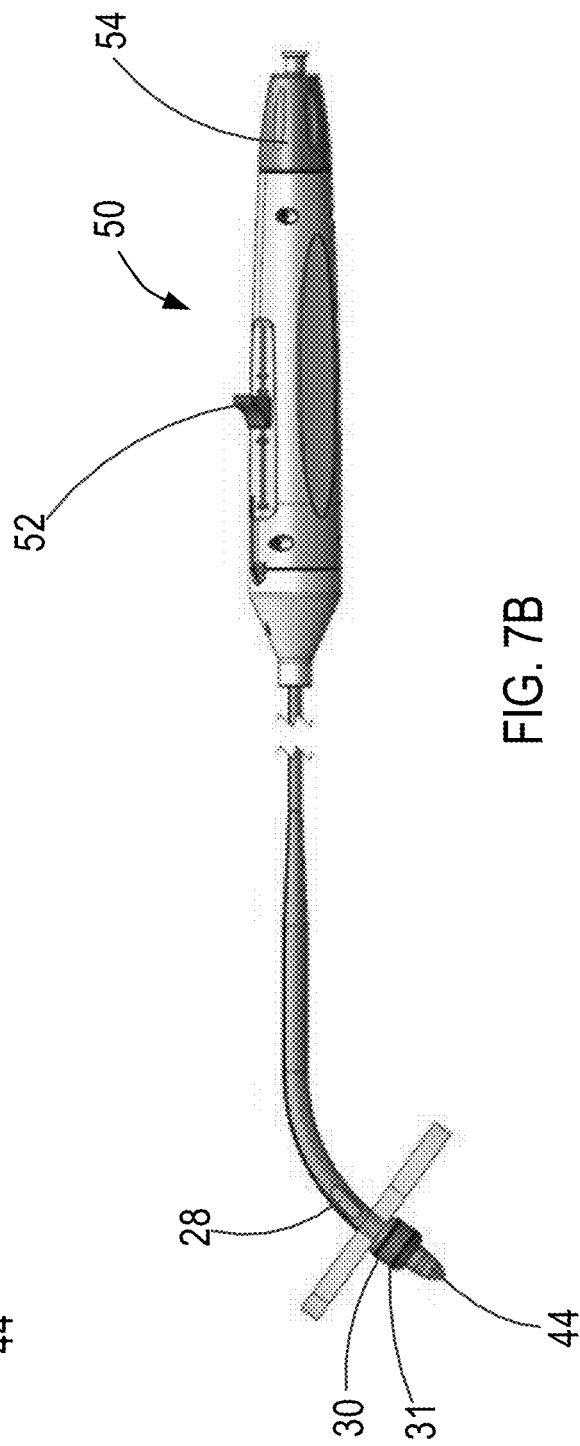
FIG. 7A
FIG. 7B

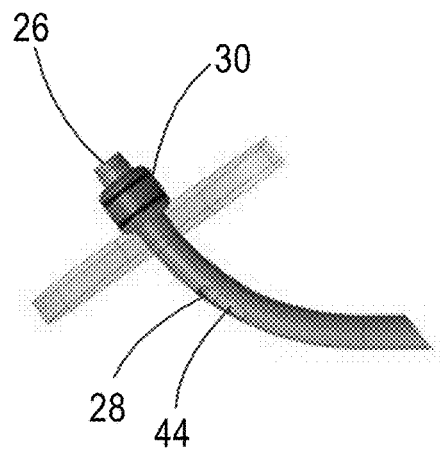
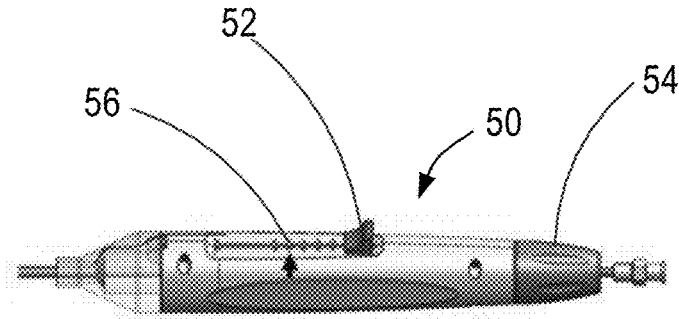
FIG. 7E
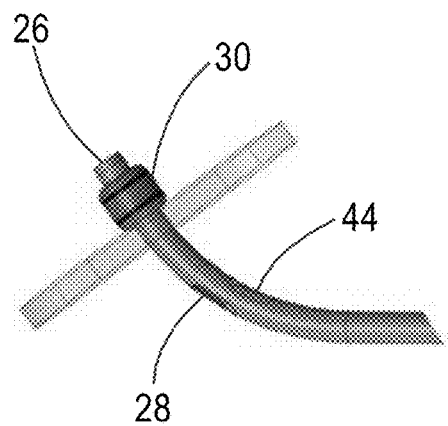
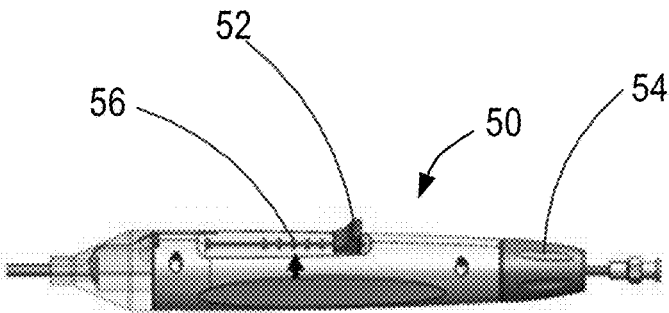
FIG. 7F
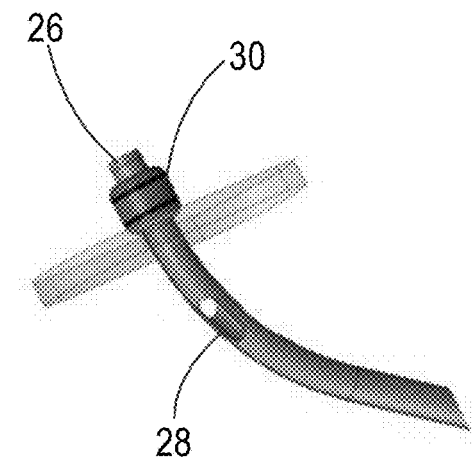
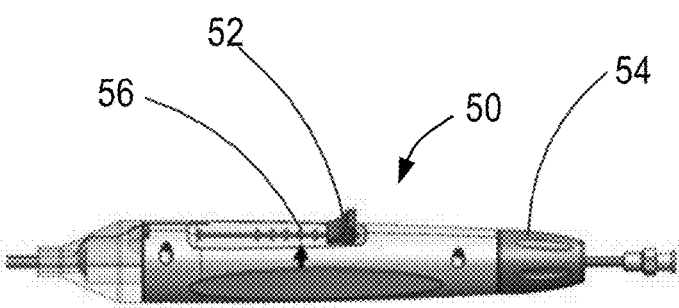
FIG. 7G

SYSTEMS AND METHODS FOR CREATING AN INTERATRIAL SHUNT

CROSS-REFERENCE TO RELATED APPLICATIONS

This application claims the benefit of priority of U.S. Provisional Patent Application No. 62/850,511, filed May 20, 2019, the entire contents of which are incorporated herein by reference.

FIELD OF THE INVENTION

This application generally relates to systems and methods for creating an interatrial shunt to redistribute blood from one cardiac chamber to another to address pathologies such as heart failure ("HF"), myocardial infarction ("MI") and pulmonary arterial hypertension ("PAH").

BACKGROUND OF THE INVENTION

Heart failure is the physiological state in which cardiac output is insufficient to meet the needs of the body or to do so only at a higher filing pressure. There are many underlying causes of HF, including myocardial infarction, coronary artery disease, valvular disease, hypertension, and myocarditis. Chronic heart failure is associated with neurohormonal activation and alterations in autonomic control. Although these compensatory neurohormonal mechanisms provide valuable support for the heart under normal physiological circumstances, they also play a fundamental role in the development and subsequent progression of HF.

For example, one of the body's main compensatory mechanisms for reduced blood flow in HF is to increase the amount of salt and water retained by the kidneys. Retaining salt and water, instead of excreting it via urine, increases the volume of blood in the bloodstream and helps to maintain blood pressure. However, the larger volumes of blood also cause the heart muscle, particularly the ventricles, to become enlarged. As the heart chambers become enlarged, the wall thickness decreases and the heart's contractions weaken, causing a downward spiral in cardiac function. Another compensatory mechanism is vasoconstriction of the arterial system, which raises the blood pressure to help maintain adequate perfusion, thus increasing the load that the heart must pump against.

In low ejection fraction ("EF") heart failure, high pressures in the heart result from the body's attempt to maintain the high pressures needed for adequate peripheral perfusion. However, as the heart weakens as a result of such high pressures, the disorder becomes exacerbated. Pressure in the left atrium may exceed 25 mmHg, at which stage, fluids from the blood flowing through the pulmonary circulatory system transudate or flow out of the pulmonary capillaries into the pulmonary interstitial spaces and into the alveoli, causing lung congestion and if untreated the syndrome of acute pulmonary edema and death.

Table 1 lists typical ranges of right atrial pressure ("RAP"), right ventricular pressure ("RVP"), left atrial pressure ("LAP"), left ventricular pressure ("LVP"), cardiac output ("CO"), and stroke volume ("SV") for a normal heart and for a heart suffering from HF. In a normal heart beating at around 70 beats/minute, the stroke volume needed to maintain normal cardiac output is about 60 to 100 milliliters. When the preload, after-load, and contractility of the heart are normal, the pressures required to achieve normal cardiac output are listed in Table 1. In a heart suffering from HF, the hemodynamic parameters change (as shown in Table 1) to maintain peripheral perfusion.

TABLE 1

| Parameter | Normal Range | HF Range |
|---|---|---|
| RAP (mmHg) | 2-6 | 6-20 |
| RVSP (mmHg) | 15-25 | 20-80 |
| LAP (mmHg) | 6-12 | 15-50 |
| LVEDP (mmHg) | 6-12 | 15-50 |
| CO (liters/minute) | 4-8 | 2-6 |
| SV (milliliters/beat) | 60-100 | 30-80 |

HF is generally classified as either systolic heart failure ("SHF") or diastolic heart failure ("DHF"). In SHF, the pumping action of the heart is reduced or weakened. A common clinical measurement is the ejection fraction, which is a function of the blood ejected out of the left ventricle (stroke volume) divided by the maximum volume in the left ventricle at the end of diastole or relaxation phase. A normal ejection fraction is greater than 50%. Systolic heart failure generally causes a decreased ejection fraction of less than 40%. Such patients have heart failure with reduced ejection fraction ("HFrEF"). A patient with HFrEF may usually have a larger left ventricle because of a phenomenon called "cardiac remodeling" that occurs secondarily to the higher ventricular pressures.

In DHF, the heart generally contracts normally, with a normal ejection fraction, but is stiffer, or less compliant, than a healthy heart would be when relaxing and filling with blood. Such patients are said to have heart failure with preserved ejection fraction ("HFpEF"). This stiffness may impede blood from filling the heart and produce backup into the lungs, which may result in pulmonary venous hypertension and lung edema. HFpEF is more common in patients older than 75 years, especially in women with high blood pressure.

Both variants of HF have been treated using pharmacological approaches, which typically involve the use of vasodilators for reducing the workload of the heart by reducing systemic vascular resistance, as well as diuretics, which inhibit fluid accumulation and edema formation, and reduce cardiac filling pressure. No pharmacological therapies have been shown to improve morbidity or mortality in HFpEF whereas several classes of drugs have made an important impact on the management of patients with HFrEF, including renin-angiotensin antagonists, beta blockers, and mineralocorticoid antagonists. Nonetheless, in general, HF remains a progressive disease and most patients have deteriorating cardiac function and symptoms over time. In the U.S., there are over 1 million hospitalizations annually for acutely worsening HF and mortality is higher than for most forms of cancer.

In more severe cases of HFrEF, assist devices such as mechanical pumps are used to reduce the load on the heart by performing all or part of the pumping function normally done by the heart. Chronic left ventricular assist devices ("LVAD"), and cardiac transplantation, often are used as measures of last resort. However, such assist devices typically are intended to improve the pumping capacity of the heart, to increase cardiac output to levels compatible with normal life, and to sustain the patient until a donor heart for transplantation becomes available. Such mechanical devices enable propulsion of significant volumes of blood (liters/min), but are limited by a need for a power supply, relatively large pumps, and pose a risk of hemolysis, thrombus formation, and infection. Temporary assist devices, intra-aortic balloons, and pacing devices have also been used.

Various devices have been developed using stents to modify blood pressure and flow within a given vessel, or between chambers of the heart. For example, U.S. Pat. No. 6,120,534 to Ruiz is directed to an endoluminal stent for regulating the flow of fluids through a body vessel or organ, for example, for regulating blood flow through the pulmonary artery to treat congenital heart defects. The stent may include an expandable mesh having lobed or conical portions joined by a constricted region, which limits flow through the stent. The mesh may comprise longitudinal struts connected by transverse sinusoidal or serpentine connecting members. Ruiz is silent on the treatment of HF or the reduction of left atrial pressure.

U.S. Pat. No. 6,468,303 to Amplatz et al. describes a collapsible medical device and associated method for shunting selected organs and vessels. Amplatz describes that the device may be suitable to shunt a septal defect of a patient's heart, for example, by creating a shunt in the atrial septum of a neonate with hypoplastic left heart syndrome ("HLHS"). That patent also describes that increasing mixing of pulmonary and systemic venous blood improves oxygen saturation, and that the shunt may later be closed with an occluding device. Amplatz is silent on the treatment of HF or the reduction of left atrial pressure, as well as on means for regulating the rate of blood flow through the device.

Implantable interatrial shunt devices have been successfully used in patients with severe symptomatic heart failure. By diverting or shunting blood from the left atrium ("LA") to the right atrium ("RA"), the pressure in the left atrium is lowered or prevented from elevating as high as it would otherwise (left atrial decompression). Such an accomplishment would be expected to prevent, relieve, or limit the symptoms, signs, and syndromes associated with pulmonary congestion. These include severe shortness of breath, pulmonary edema, hypoxia, the need for acute hospitalization, mechanical ventilation, and death.

Shunt flow is generally governed by the pressure gradient between the atria, and by the fluid mechanical properties of the shunt device. The latter are typically affected by the shunt's geometry and material composition. For example, the general flow properties of similar shunt designs have been shown to be related to the mean interatrial pressure gradient and the effective orifice diameter.

Percutaneous implantation of interatrial shunts generally requires transseptal catheterization immediately preceding shunt device insertion. The transseptal catheterization system is placed, from an entrance site in the femoral vein, across the interatrial septum in the region of fossa ovalis ("FO"), which is the central and thinnest region of the interatrial septum. This is the same general location where a congenital secundum atrial septal defect ("ASD") would be located. The FO in adults is typically 15-20 mm in its major axis dimension and <3 mm in thickness, but in certain circumstances may be up to 10 mm thick. LA chamber access may be achieved using a host of different techniques familiar to those skilled in the art, including but not limited to: needle puncture, stylet puncture, screw needle puncture, and radiofrequency ablation. The passageway between the two atria is dilated to facilitate passage of a shunt device having a desired orifice size. Dilation generally is accomplished by advancing a tapered sheath/dilator catheter system or inflation of an angioplasty-type balloon across the FO.

U.S. Patent Publication No. 2005/0165344 to Dobak, III describes apparatus for treating heart failure that includes a tubular conduit having an emboli filter or valve, the device configured to be positioned in an opening in the atrial septum of the heart to allow flow from the left atrium into the right atrium. Dobak discloses that shunting of blood may reduce left atrial pressures, thereby preventing pulmonary edema and progressive left ventricular dysfunction, and reducing LVEDP. Dobak describes that the device may include deployable retention struts, such as metallic arms that exert a slight force on the atrial septum on both sides and pinch or clamp the device to the septum.

U.S. Pat. No. 9,034,034 to Nitzan, the entire contents of which are incorporated by reference herein, describes a shunt comprising an hourglass or diabolo outer shape, having a small FO footprint minimizing septal injury, which is expected to minimize pannus growth and obliteration of the shunt lumen. Its one-way valve also is designed to reduce the potential for reverse shunting and paradoxical embolization. The relatively small footprint of the shunt in contact with the septum and encapsulated collapsible nitinol frame is designed to facilitate percutaneous extraction from the septum and retrieval from the body using a standard goose-neck snare and large-bore sheath, thus making the device more easily retrieved. The venturi tube-like inner lumen of the diabolo shape provides better bulk flow characteristics, permitting a smaller orifice for the same amount of flow compared to orifice-plate shunts. And finally, the small footprint on the FO and the hourglass shape are designed to facilitate accurate placement and retention during implantation. This geometry also minimizes interference with normal motion of the interatrial septum, and the small footprint provides space surrounding the shunt for other potential interventional procedures that require transseptal catheterization.

One embodiment of the Nitzan design, manufactured by V-Wave, Ltd (Caesarea, Israel), designed to support unidirectional left-to-right flow, comprises a self-expanding frame constructed from a laser-cut nitinol tube. The frame includes five sinusoidal circumferential struts interconnected by six longitudinal bars. The frame is heat-set so that it has an asymmetrical hourglass shape or a diabolo shape. The shunt is deployed so that the neck (5.3 mm outer diameter) is placed across the FO and secured in place by its external surface geometry. The shunt's widest portion has a conical shape with an approximately 14.3 mm outer diameter at the LA end of the shunt, which serves as an "entry" port on the distal end of the entry funnel. The entry funnel is deployed in the left atrium, and registers the neck of the shunt to the region of the FO. A second, slightly narrower bell-shaped portion forms the exit portion of the shunt, which expands to a maximum outer diameter of 11.4 mm at the RA end of the shunt. The shunt does not require flanges, discs, or tissue anchors to secure it in place. Septal retention is achieved without applying persistent pressure, tension or rubbing contact on the tissue adjoining the device neck.

The V-Wave shunt has a single inner lumen where flow is entrained into the entry funnel in the LA and passes through the constricted neck having a 5.1 mm inner diameter, which resembles a venturi-type orifice, and then exits through a bioprosthetic valve positioned near the RA end of the shunt. The entry funnel and the central neck region are encapsulated with expanded polytetrafluoroethylene ("ePTFE") to form a skirt or cover over the frame. The skirt is designed to facilitate laminar flow and limit pannus ingrowth during device healing. The exit bell-shaped portion contains three, glutaraldehyde-fixed, porcine pericardial leaflets sutured to the frame at the right atrial extent of the ePTFE encapsulation. The leaflets are designed to create a smooth exit channel and remain in the open position, closing only when the RA pressure exceeds LA pressure by 1-2 mmHg, thus preventing reverse right-to-left shunting.

U.S. Pat. Nos. 10,076,403 and 10,251,740 to Eigler, the entire contents of each of which are incorporated by reference herein, describe an interatrial shunt designed for regulating blood pressure between a patient's left and right atrium, while preventing pannus formation from narrowing the lumen in the neck region of the shunt.

The size of the shunt, e.g., the diameter of the passageway through which blood flows between the left and right atrium, may have different effects on the patient's hemodynamics and systemic oxygen delivery. For example, too small a shunt will have no benefit, whereas too large a shunt may diminish systemic oxygen deliver due to too large an admixture of desaturate blood in patient with PAH, or create right-sided volume overload and right ventricular failure in a patient with left ventricular HF. In addition, each patient's physiology is unique and thus, each patient may require a specific sized interatrial shunt for optimal treatment.

Therefore, it is desirable to provide devices and methods for creating an interatrial shunt and determining the proper implantable shunt size for each individual patient prior to implanting the permanent shunt within the patient's interatrial septum.

SUMMARY OF THE INVENTION

The present invention provides systems, devices, and methods for control of blood flow across a patient's interatrial septum. An exemplary device includes a sheath having a proximal region, a distal region and a lumen therebetween. The distal region of the sheath includes a first set of one or more openings and a second set of one or more openings spaced apart from the first set of one or more openings a distance greater than a thickness of the interatrial septum such that the first set of one or more openings is disposed within a first atrium of the patient while the second set of one or more openings is disposed in a second atrium of the patient. For example, the second set of one or more openings of the sheath may have at least one of a circular, elliptical, or rectangular shape, or any combination thereof. In addition, the second set of one or more openings of the sheath may be distributed symmetrically or asymmetrically about an outer surface of the sheath.

The device further includes an actuator for modifying an area of an opening of the second set of one or more openings of the sheath, such that blood is permitted to flow between the first and second atria responsive to a pressure gradient across the interatrial septum via the first and second sets of one or more openings and the sheath lumen therebetween, at a blood flow rate corresponding with the area of the opening of the second set of one or more openings of the sheath. For example, the actuator may be actuated to incrementally select the area of the opening of the second set of one or more openings of the sheath, such that the blood flow rate of the blood flow between the first and second atria at each increment corresponds with blood flow through a predetermined sized puncture of the patient's interatrial septum, e.g., having a diameter between 4 to 8 mm.

Further, the device may include an inner sleeve moveably disposed within the lumen of the sheath. The inner sleeve has a proximal region and a distal region having an outer diameter equal to an inner diameter of the sheath. Accordingly, the actuator may be actuated to modify the area of the opening of the second set of one or more openings of the sheath by moving the inner sleeve relative to the sheath by an incremental amount such that blood is permitted to flow between the first and second atria responsive to a pressure gradient across the interatrial septum via the first and second sets of one or more openings and the sheath lumen therebetween, at a blood flow rate corresponding with the area of the opening of the second set of one or more openings of the sheath.

In addition, the inner sleeve further may include one or more flushing ports in fluid communication with a source of flushing fluid via one or more flushing lumens of the inner sleeve. Thus, the one or more flushing ports may eject the flushing fluid therethrough to prevent accumulation of blood clots at the second set of one or more openings of the sheath. Moreover, the inner sleeve may include a guidewire lumen sized and shaped for receiving a guidewire. Accordingly, the device further may include a pressure sensor guidewire that may be disposed within the guidewire lumen of the inner sleeve. The pressure sensor guidewire may be operatively coupled to an external controller, and may measure pressure within the first atrium and transmit a signal indicative of the measured pressure to the external controller.

In accordance with one aspect of the present invention, the inner sleeve moveably disposed within the lumen of the sheath has a first set of one or more apertures in fluid communication with the first set of one or more openings of the sheath, and a lumen extending therebetween. The inner sleeve further includes a second set of one or more apertures sized and shaped to register with the second set of one or more openings of the sheath. Accordingly, the actuator may be actuated to modify the area of the opening of the second set of one or more openings of the sheath by moving the inner sleeve relative to the sheath to register the second set of one or more apertures of the inner sleeve with the second set of one or more openings of the sheath by a predetermined amount such that blood is permitted to flow between the first and second atria responsive to a pressure gradient across the interatrial septum via the first and second sets of one or more openings and apertures and the inner sleeve lumen therebetween, at a blood flow rate corresponding with the predetermined amount of registration between the second set of one or more apertures of the inner sleeve and the second set of one or more openings of the sheath.

Moreover, the sheath further may include a third set of one or more openings spaced apart from the second set of one or more openings such that the third set of one or more openings is disposed within an inferior vena cava of the patient while the first set of one or more openings is disposed in the first atrium during operation of the device. Accordingly, the inner sleeve further includes a third set of one or more apertures sized and shaped to register with the third set of one or more openings of the sheath. Thus, the actuator may be actuated to move the inner sleeve relative to the sheath to register the third set of one or more apertures of the inner sleeve with the third set of one or more openings of the sheath by a predetermined amount such that blood is permitted to flow between the inferior vena cava and the first atrium responsive to a pressure gradient between the inferior vena cava and the first atrium via the first and third sets of one or more openings and apertures and the inner sleeve lumen therebetween. For example, when the third set of one or more apertures completely registers with the third set of one or more openings of the sheath, the second set of one or more apertures of the inner sleeve are not registered with the second set of one or more openings of the sheath, such that blood is permitted to flow between the inferior vena cava and the first atrium, though not between the second atrium and the inferior vena cava.

The device further may include one or more sensors disposed within the lumen of the sheath and operatively coupled to an external controller. The external controller may include a display and/or user interface such that a physician may manually operate the device. The one or more sensors may measure one or more physiological parameters, e.g., pressure, blood flow rate, blood flow velocity, or oximetry, and transmit a signal indicative of the measured physiological parameter to the external controller. Moreover, the device may include an anchor disposed at the distal region of the sheath for facilitating fixation of the sheath to the patient's interatrial septum. For example, the anchor may be a balloon that may be inflated within the first atrium, thereby preventing proximal movement of the sheath relative to the patient's interatrial septum. Alternatively, the anchor may be a balloon that may be inflated within the second atrium, thereby preventing distal movement of the sheath relative to the patient's interatrial septum. In one embodiment, the anchor may include a first balloon in the first atrium and a second balloon in the second atrium, such that when inflated, the balloons sandwich the interatrial septum. Moreover, the balloon(s) may include a metal coil disposed on its outer surface for transmitting RF energy sufficient to ablate tissue adjacent to the metal coil. Alternatively, or additionally, the anchor may include deployment tines sized and shaped to register on the wall of interatrial septum.

In accordance with one aspect of the present invention, the device may include a metal coil disposed on an outer surface of the sheath. For example, the metal coil may be disposed on the outer surface of the sheath proximal to the second set of one or more openings. The metal coil may emit RF energy sufficient to ablate tissue adjacent to the metal coil to induce an interatrial shunt.

In one embodiment, the device may include one or more additional metal coils, such that each of the metal coils may emit RF energy sufficient to ablate tissue adjacent to the respective metal coil to induce an interatrial shunt having a predetermined diameter. For example, a graded portion of the sheath may have an outer surface having a cross-sectional area that increases in a distal direction, such that each of the metal coils are disposed along the graded portion of the sheath at a position corresponding the predetermined diameter.

In accordance with another aspect of the present invention, a method for controlling blood flow across a patient's interatrial septum is provided. The method may include creating a puncture through the patient's interatrial septum; delivering the sheath across the puncture such that the first set of one or more openings of the sheath is disposed within a first atrium of the patient and the second set of one or more openings of the sheath is disposed within a second atrium of the patient; permitting blood to flow between the first and second atria responsive to a pressure gradient across the interatrial septum via the first and second set of one or more openings and a lumen of the sheath; modifying an area of an opening of the second set of one or more openings such that blood is permitted to flow between the first and second atria via the first and second set of one or more openings and a lumen of the sheath at a modified blood flow rate; and selecting an interatrial shunt for implantation in the patient's interatrial septum based on the permitting and the modifying.

For example, modifying the area of the opening of the second set of one or more openings may include moving the inner sleeve within the lumen of the sheath by an incremental amount, such that blood is permitted to flow between the first and second atria via the first set of one or more openings of the sheath and the opening provided between the second set of one or more openings of the sheath and the distal region of the inner sleeve at a blood flow rate corresponding with the area of the opening of the second set of one or more openings.

Additionally, the method may include emitting RF energy to ablate tissue surrounding the puncture to alter tissue healing. For example, emitting RF energy to ablate tissue surrounding the puncture may induce an interatrial shunt having a predetermined diameter. Accordingly, the method further may include moving the sheath relative to the interatrial septum to align the interatrial septum with a metal coil disposed on an outer surface of the sheath, such that emitting RF energy to ablate tissue surrounding the puncture includes emitting RF energy via the metal coil to ablate tissue surrounding the puncture to induce the interatrial shunt having the predetermined diameter.

When the patient has pulmonary arterial hypertension, blood is permitted to flow from within the right atrium to the left atrium responsive to a pressure gradient across the interatrial septum via the first and second set of one or more openings of the sheath and the sheath lumen. When the patient has heart failure, blood is permitted to flow from within the left atrium to the right atrium responsive to a pressure gradient across the interatrial septum via the first and second set of one or more openings of the sheath and the sheath lumen.

The method further includes measuring blood flow rate of the blood flow between the first and second atrium, and/or measuring at least one physiological parameter of the patient at each incremental area of the opening of the second set of one or more openings. In accordance with one aspect of the present invention, a signal indicative of the measured physiological parameter may be transmitted to an external controller or display. In another aspect of the present invention, measuring at least one physiological parameter of the patient may be performed by a separate system, such as a cardiac ultrasound machine, pulse oximeter, electrocardiogram, sphygmomanometer or forms of hemodynamic monitoring known to those skilled in the art of patient physiology. Accordingly, the implantable interatrial shunt provided may have a preselected diameter at its neck region based on the signal indicative of the measured physiological parameter.

BRIEF DESCRIPTION OF DRAWINGS

FIG. 1B is a schematic of an exemplary system including the device of FIG. 1A.

FIGS. 5A and 5B illustrate an exemplary handle of the device of FIG. 1 constructed in accordance with the principles of the present invention.

FIGS. 7A to 7I illustrate the steps of the exemplary method of FIG. 6 in accordance with the principles of the present invention.

DETAILED DESCRIPTION

Interatrial shunts, such as those manufactured by V-Wave, Ltd. (Caesarea, Israel), may be used to redistribute blood from one cardiac chamber to another to address pathologies such as heart failure, myocardial infarction and pulmonary arterial hypertension (PAH). For example, in patients with PAH, an interatrial shunt permits blood to flow from the right atrium across the interatrial septum to the left atrium to treat acute right ventricular heart failure. A correctly sized shunt will decompress the right ventricle and improve total systemic oxygen delivery, whereas too small a shunt could have minimal benefit, and too large a shunt could diminish systemic oxygen delivery due to too large an admixture of desaturated blood.

In patients with left ventricular HF, an interatrial shunt permits blood to flow from the left atrium across the interatrial septum to the right atrium to treat acute left ventricular heart failure due to, e.g., worsening of chronic HF or acute decompensation of the LV following an insult such as acute myocardial infarction resulting in severe pump failure or acute mitral valve regurgitation such as occurs with papillary muscle dysfunction or chordal rupture. A correctly sized shunt will decompress the left ventricle and left atrium and relieve pulmonary congestion without creating RV volume overload, whereas too small a shunt could have minimal benefit, and too large a shunt could create right-sided volume overload and RV failure.

In patients with more stable PAH or chronic HF, the information gained about hemodynamic responses during temporary precision shunting can be used to guide the sizing of a permanent interatrial shunt, whether it be by placement of an implantable interatrial device or creation of an iatrogenic atrial septal defect.

Figure 1A:
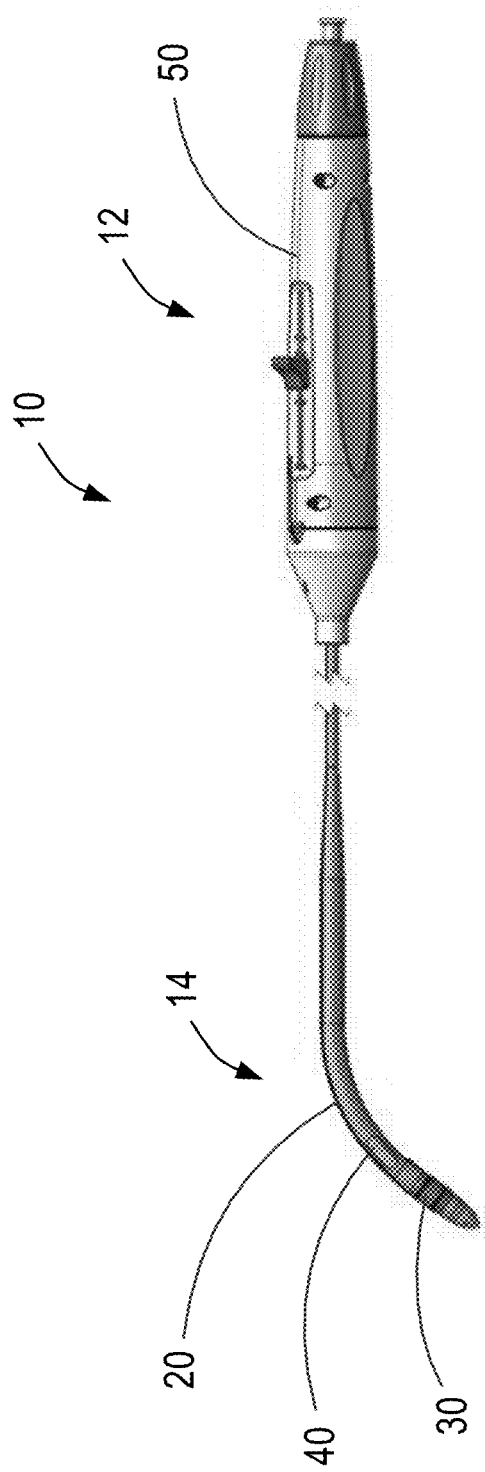
FIG. 1A illustrates an exemplary device for temporary precision shunting constructed in accordance with the principles of the present invention.

Referring now to FIG. 1A, exemplary sheath-shunt prototype device, e.g., device 10, for temporary precision shunting is provided. Device 10 includes proximal region 12 and distal region 14 sized and shaped to be delivered within a patient, e.g., between two heart chambers such as the left and right atrium. Device 10 includes sheath 20 and inner sleeve 40 moveably disposed within a lumen of sheath 20. Sheath 20 may include anchor 30 for fixing sheath 20 relative to the patient's interatrial septum during operation of device 10 as described in further detail below.

Sheath 20 and inner sleeve 40 extend from distal region 14 of device 10 to proximal region 12 where sheath 20 and inner sleeve 40 are operatively coupled to actuator 50, external to the patient's body. Actuator 50, e.g., a handle, may be selectively actuated to incrementally move inner sleeve 40 relative to sheath 20 to precisely control the amount and rate of blood flow permitted to flow through sheath 20 from one heart chamber to the other depending on the pressure gradient across the interatrial septum. Accordingly, device 10 may simulate blood flow corresponding to the blood flow through interatrial shunts of various sizes. The patient's hemodynamics responsive to the various size shunt simulations may be monitored to determine the most effective shunt size for a specific patient. For example, the correlation between the flowrates measured in-vivo through device 10 and the corresponding flowrates through the interatrial shunts of various sizes may be based on a series of in-vitro comparative simulations under various pressure gradients. In addition, the correlation may be represented in a lookup table and/or stored in a memory of an external controller.

For example, as shown in FIG. 1B, device 10 further may include one or more sensors 21 coupled to sheath 20, e.g., disposed within the lumen of sheath 20, for measuring one or more physiological parameters including at least one of pressure, blood flow rate, blood flow velocity, or oximetry. Sensors 21 generate and transmit signal(s) indicative of the measured physiological parameter(s) to external controller 55 operatively coupled to one or more sensors 21. Controller 55 may store and monitor the patient's hemodynamics based on the measured physiological parameter(s) such that a physician may determine the shunt size best suited for each specific patient. For example, controller 55 may store predetermined thresholds of desired patient hemodynamics in memory of controller 55, such that controller 55 may compare the measured physiological parameter(s) at each simulated shunt size with the predetermined thresholds to determine which shunt size would provide the most desirable results for the patient.

Figure 2A:
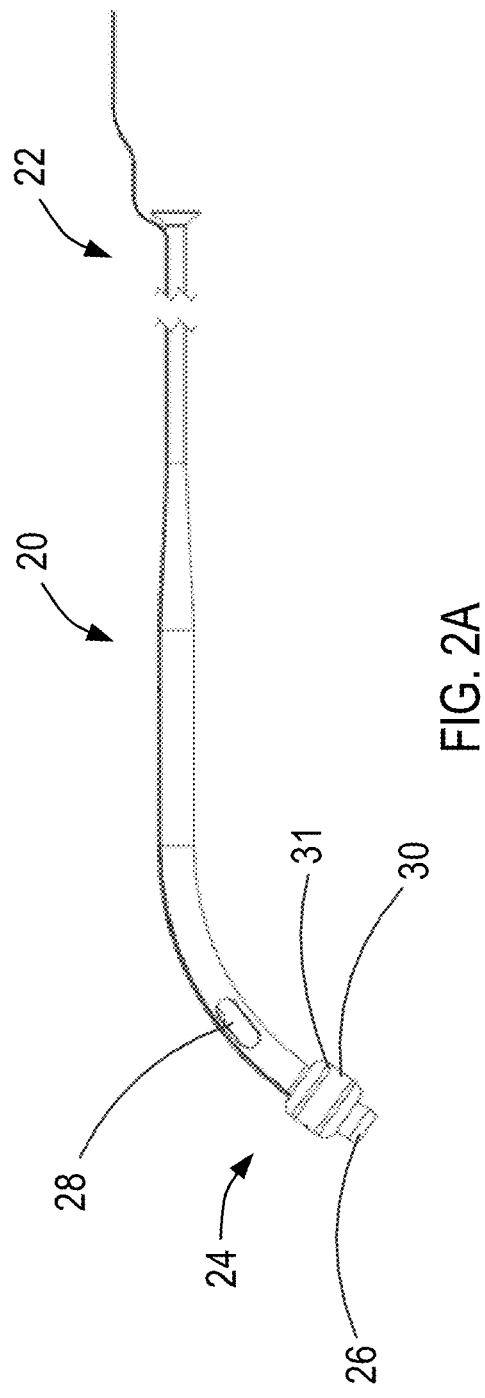
FIG. 2A illustrates an exemplary sheath of the device of FIG. 1 constructed in accordance with the principles of the present invention.

Referring now to FIG. 2A, exemplary sheath 20 is provided. Sheath 20 may be made of a biocompatible polymer such as Pebax, Nylon, etc., or high-density polyethylene ("HDPE"). Preferably sheath 20 is made of Pebax. Sheath 20 may have a radiopaque marker band for optimal positioning verification during delivery of sheath 20 to, e.g., the patient's interatrial septum. Sheath 20 has proximal region 22 for coupling with actuator 50, and distal region 24 sized and shaped to be positioned within the patient's body, e.g., across a puncture of the patient's interatrial septum. In accordance with one aspect of the present invention, sheath 20 may have a tapered geometry such that proximal region 22 of sheath 20 has an outer diameter that is smaller than the rest of the sheath's length, e.g., distal region 24 of sheath 20. Accordingly, the differentiation in outer diameter size along sheath 20 may minimize trauma to the access site, and potentially allow longer catheter dwell time. Alternatively, sheath 20, and accordingly the inner sleeve, may have a constant diameter from proximal region 22 to distal region 24.

As illustrated in FIG. 2A, sheath 20 has a first set of one or more openings 26 at its distal end, and a second set of pre-cut features, e.g., one or more openings 28 disposed along sheath 20 at a position proximal to the first set of one or more openings 26. The second set of one or more openings 28 is positioned a distance from the first set of one or more openings 26 greater than a thickness of the interatrial septum such that while one or more openings 26 is disposed in, e.g., a first atrium, one or more openings 28 are disposed in, e.g., a second atrium. For example, one or more openings 26 may be disposed within the patient's left atrium while one or more openings 28 are disposed within the patient's right atrium, or vice versa. One or more openings 28 are in fluid communication with one or more openings 26 of sheath 20 via a lumen of sheath 20, thereby permitting blood to flow between the patient's right and left atria responsive to a pressure gradient across the interatrial septum via one or more openings 26 and 28 when one or more openings 28 are not obstructed as described in further detail below, and the sheath's lumen. For example, in patients with PAH, blood is permitted to flow from the patient's right atrium, through an opening of one or more openings 28 into the sheath's lumen, and exit through one or more openings 26; whereas in patients with left ventricular HF, blood is permitted to flow from the patient's left atrium, through one or more openings 26 into the sheath's lumen, and exit through an opening of one or more openings 28.

In another embodiment, the sheath may be manufactured from a polymer which enables its radial expansion subject to balloon inflation, thereby enabling an increase of shunted blood flow. Accordingly, the sheath may be further adjustable via subsequent inflation/deflation of the sheath. Further, sheath 20 may be delivered via the right femoral vein over a guidewire following traditional standard transseptal catheterization. Alternatively, sheath 20 may be delivered via a venous access site once a guidewire pathway to the left atrium has been established by other means.

As illustrated in FIG. 2A, sheath 20 may include anchor 30, e.g., a septal fixation element, for anchoring sheath 20 relative to, e.g., the patient's interatrial septum, during operation of device 10 to stabilize sheath 20 during retraction of inner sleeve 40. For example, anchor 30 may be an inflatable balloon mounted on the outer surface of sheath 20 at distal region 24. Balloon 30 may have a waist section, for self-registration on the interatrial septum. Balloon 30 may be inflated via an inflation lumen of sheath 20 in fluid communication with the internal space of the balloon and a fluid inflation source. Balloon 30 enables fixation of sheath 20 at the target site, as well as ensures optimal positioning of sheath 20 with respect to the interatrial septum, e.g., one or more openings 26 are located in the mid-LA and one or more openings 28 are located in mid-RA. Balloon 30 may be inflated such that it is disposed on one side of the interatrial septum, or alternatively, on both sides of the interatrial septum such that the balloon sandwiches the interatrial septum for improved fixation as described in further detail below with regard to FIG. 9. For example, when balloon 30 is inflated such that balloon 30 is positioned entirely within the patient's right atrium, sheath 20 will be prevented from moving distally toward the patient's left atrium. Alternatively, when balloon 30 is inflated such that balloon 30 is positioned entirely within the patient's left atrium, sheath 20 will be prevented from moving proximally toward the patient's right atrium. As will be understood by a person having ordinary skill in the art, balloon 30 may be sized and shaped accordingly to anchor sheath 20 within the puncture of the interatrial septum.

In accordance with another aspect of the present invention, anchor 30 may include a series of septal fixation elements such as deployable tines designed to be delivered to the interatrial septum in a contracted delivery state, and expanded, e.g., upon retracted of an introductory sheath, to an expanded, deployed state to anchor sheath 20 to the interatrial septum. Other septal fixation elements may be affixed to the distal region of sheath 20 to anchor sheath 20 to the interatrial septum including, for example, the septal fixation elements described in U.S. Pat. Nos. 9,943,670, 8,328,751, and 8,091,556 to Keren, U.S. Pat. Nos. 9,724,499 and 8,070,708 to Rottenberg, and U.S. Pat. No. 9,681,948 to Levi, the entire contents of each of which are incorporated herein by reference.

In accordance with one aspect of the present invention, sheath 20 may have metal coil 31 capable of transmitting RF energy disposed on its external surface, for ablating the contour of the puncture within the patient's fossa ovalis. As shown in FIG. 2A, coil 31 may be disposed on the outer surface of balloon 30, thereby forming a hot balloon such as those described in, e.g., U.S. Pat. No. 5,578,008 to Hara and U.S. Patent Application No. 2010/0069836 to Satake, the entire contents of each of which are incorporated by reference herein. Accordingly, balloon 30 may be used to heat the tissue contouring the puncture within the interatrial septum to ablate the tissue to alter tissue healing to prevent or limit proliferate tissue ingrowth in response to mechanical injury.

Figure 2B:
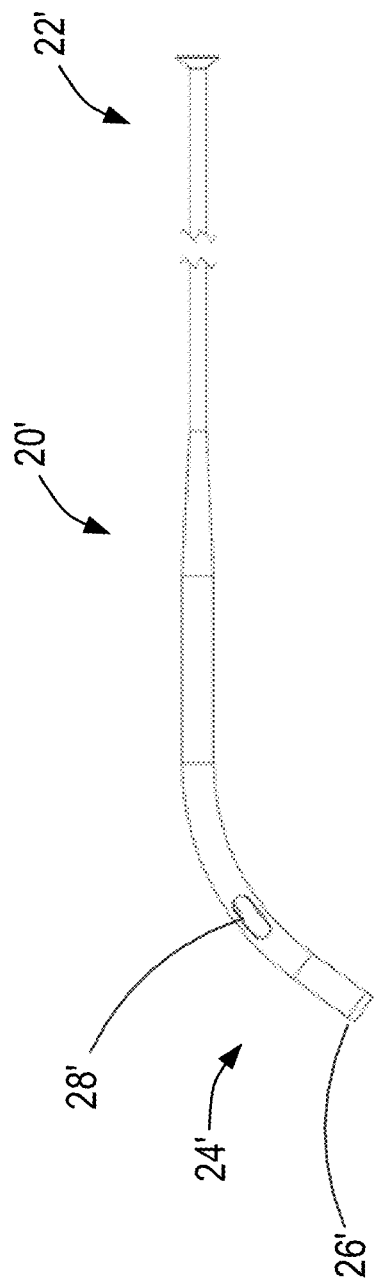
FIG. 2B illustrates an alternative exemplary sheath constructed in accordance with the principles of the present invention.

Referring now to FIG. 2B, an alternative exemplary sheath is provided. Sheath 20' is constructed similarly to sheath 20 of FIG. 2A wherein like components are identified by like-primed reference numbers. For example, proximal region 22' corresponds with proximal region 22, distal region 24' corresponds with distal region 24, one or more openings 26' correspond with one or more openings 26, and one or more openings 28' correspond with one or more openings 28. Sheath 20' differs from sheath 20 in that sheath 20' does not include optional anchor 30 disposed on distal region 24'. As will be understood by a person of ordinary skill in the art, the sheath, and accordingly the inner sleeve, may have a constant diameter from the proximal region to the distal region.

Referring now to FIGS. 3A to 3D, various configurations of the pre-cut features of the second set of one or more openings of the sheath are provided. One or more openings 28, 28' may have a shape selected from oval, circular, rectangular, etc., adapted to provide minimal resistance to flow, i.e., low shear stress and low turbulence, and controlled flowrate by enabling gradual exposure of the one or more openings subject to actuation of actuator 50 as described in further detail below. The disposition and arrangement of the one or more openings may be selected to optimize flow, as well as to maintain structural integrity and functionality of the sheath. The one or more openings may be manufactured using laser-cutting, mechanical puncturing, etc. In accordance with some aspects of the present invention, the one or more openings may include a mesh, e.g., made of a very thin braid of nitinol wires, to prevent passage of emboli therethrough.

Figure 3A:
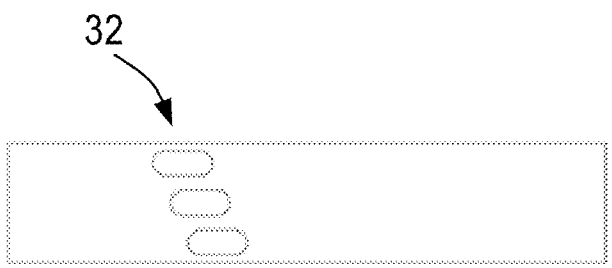
FIGS. 3A to 3D illustrate various configurations of one or more openings of the sheath constructed in accordance with the principles of the present invention.
Figure 3B:
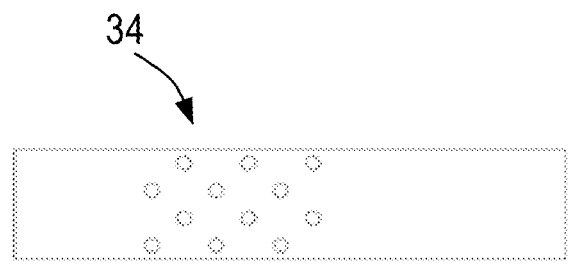
Figure 3C:
Figure 3D:
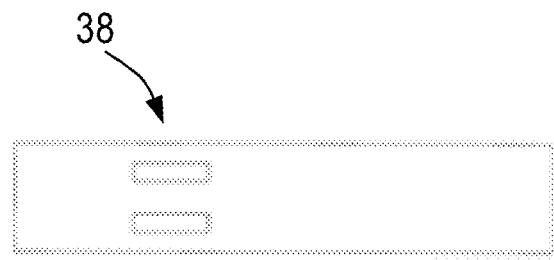

As shown in FIG. 3A, one or more openings 32 have an oval shape and are distributed along the distal region of the sheath in a coil-like pattern such that at least one opening of the one or more openings is positioned more proximal than another one of the one or more openings. As shown in FIG. 3B, one or more openings 34 may have a circular shape, and as shown in FIG. 3C, one or more openings 36 may have a rectangular shape. As shown in FIG. 3C, one or more openings 36 may be distributed equally along a single plane perpendicular to the longitudinal axis of the sheath. The openings may be distributed symmetrically or asymmetrically about the outer surface of sheath 20. As shown in FIG. 3D, the sheath includes four longitudinal openings 38 (two openings not shown) evenly spaced around the circumference of the sheath As will be understood by a person having ordinary skill in the art, more or less openings may be formed along the distal region of the sheath than as shown in FIGS. 3A to 3D.

Figure 4A:
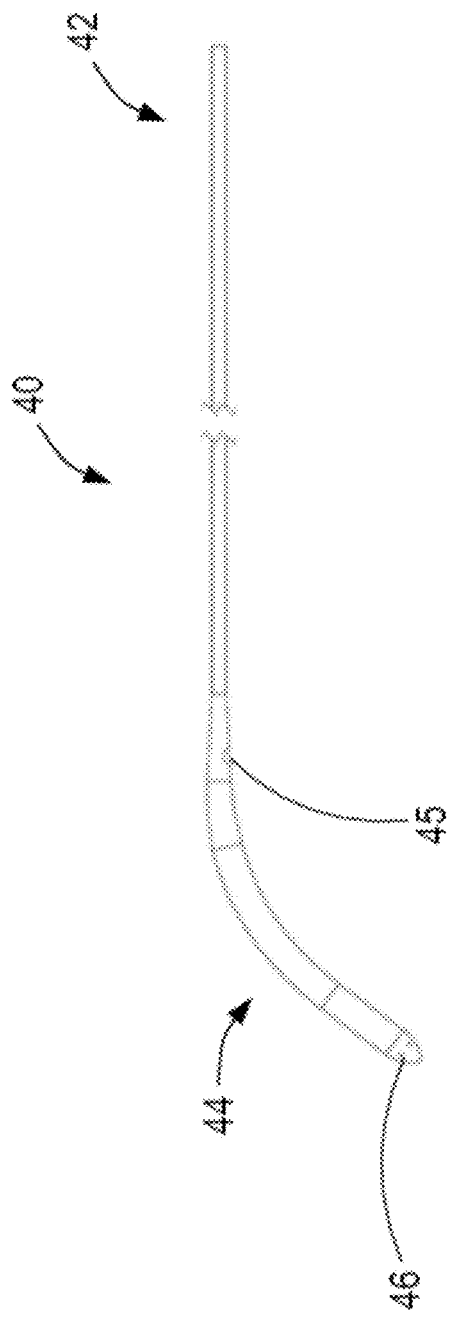
FIG. 4A illustrates an exemplary inner sleeve of the device of FIG. 1 constructed in accordance with the principles of the present invention.
Figure 4B:
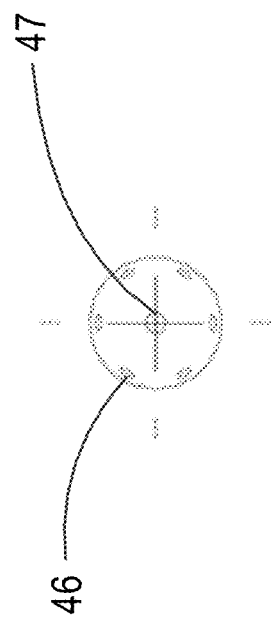
FIG. 4B illustrates the flushing ports of the inner sleeve of FIG. 4A.

Referring now to FIGS. 4A and 4B, exemplary inner sleeve 40 is provided. Inner sleeve 40 may be made of a biocompatible polymer such as Pebax, Nylon, etc., or high-density polyethylene ("HDPE"). Preferably inner sleeve 40 is made of Pebax. In addition, inner sleeve 40 may have a stiffness sufficient to maintain the puncture within the interatrial septum when disposed within sheath 20 across the interatrial septum. Inner sleeve 40 may have a radiopaque marker band for optimal positioning verification when positioning inner sleeve 40 within the lumen of sheath 20. Inner sleeve 40 has proximal region 42 for coupling with actuator 50, and distal region 44 sized and shaped to be moveably disposed within the lumen of sheath 20.

As shown in FIGS. 4A and 4B, inner sleeve 40 may have one or more flushing ports 46 disposed at distal region 44, and in fluid communication with a flushing fluid source external to the patient's body. Accordingly, flushing fluid may be ejected via one or more flushing ports 46 during operation of device 10 to prevent accumulation of blood clots at one or more openings 26 and/or one or more openings 28 of sheath 20. In addition, inner sleeve 40 may have guidewire lumen 47 for receiving a guidewire therein during delivery of inner sleeve 40 within sheath 20.

Figure 2C:
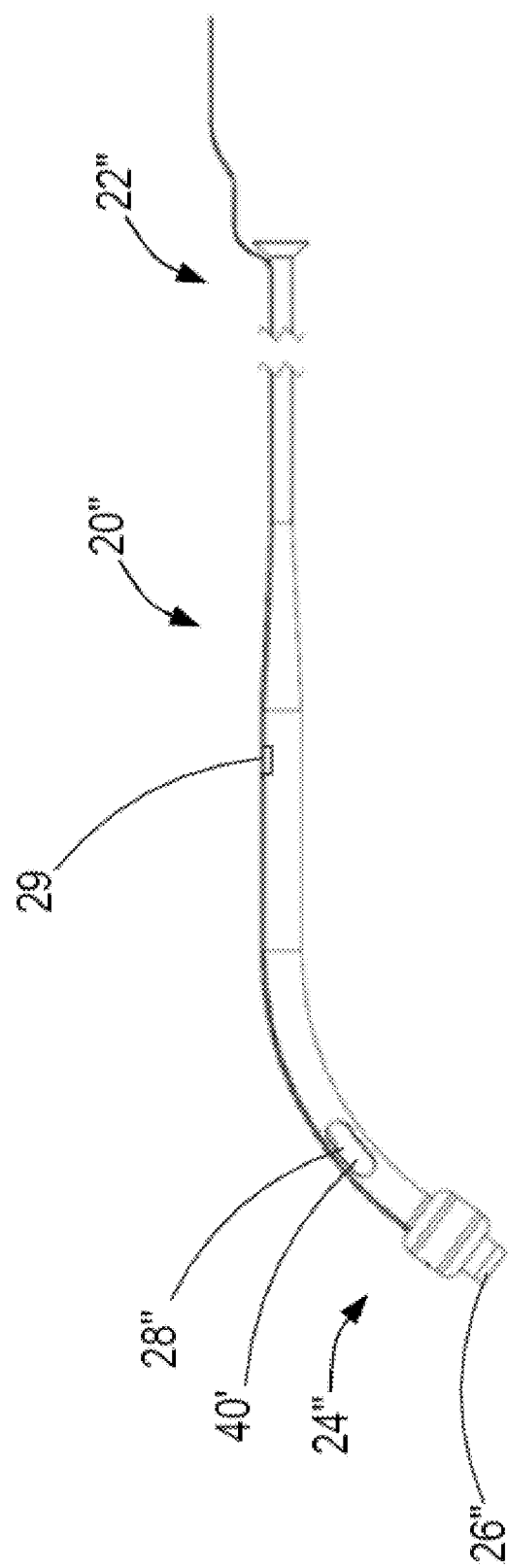
FIG. 2C illustrates another alternative exemplary sheath constructed in accordance with the principles of the present invention.

Inner sleeve 40 may have a tapered geometry corresponding with sheath 20 as described above. Accordingly, when both the sheath and inner sleeve have corresponding tapered geometries, as illustrated in FIG. 2C, sheath 20" may include one or more vents 29, e.g., one or more openings, adjacent to the tapered section along sheath 20" to permit the displacement of fluid into or out of the changing volume between the two tapered tubes sheath 20" and inner sleeve 40'. In addition, as illustrated in FIG. 4A, inner sleeve 40 may include one or more flushing vents 45, e.g., one or more openings, positioned on the proximal portion of the tapered section along inner sleeve 40 and in fluid communication with a flushing fluid source external to the patient's body. Accordingly, flushing fluid, e.g., heparinized saline, may be ejected via one or more flushing vents 45 during operation of device 10 to prevent accumulation of thrombus at one or more vents 29 of sheath 20". Alternatively, in the embodiment where the sheath has a constant diameter from the proximal region to the distal region as described above, inner sleeve 40 also may have a constant diameter from proximal region 42 to distal region 44.

By comparing FIG. 2C with FIG. 4A, one or more flushing vents 45 may be positioned circumferentially about inner sleeve 40 such that one or more flushing vents 45 are opposite circumferentially to one or more vents 29 of sheath 20" to allow for more complete flushing of the space between inner sleeve 40 and sheath 20". Accordingly, one or more vents 29 and one or more flushing vents 45 will allow flow between one or more flushing ports 46 at the distal tip of inner sleeve 40 and one or more flushing vents 45. One or more vents 29 and one or more flushing vents 45 may have a smaller opening area than one or more openings 28" and may present a small constant baseline flow between the first and second atria, such that the baseline flow may be included in the calibration of device 10.

Referring again to FIGS. 4A and 4B, at least distal region 44 of inner sleeve 40 may have an outer diameter that is essentially equal to the diameter of the inner surface of the lumen of at least distal region 24 of sheath 20 such that blood may not flow between the outer surface of inner sleeve 40 and the inner surface of sheath 20. Accordingly, when inner sleeve 40 is positioned within the lumen of sheath 20 adjacent to one or more openings 28, the opening of one or more openings 28 is obstructed and blood is not permitted to enter via one or more openings 28. Further, as inner sleeve is moved proximally relative to sheath 20 via actuator 50, the area of the opening of one or more openings 28 increases incrementally from complete obstruction to complete exposure. Thus, the area of the opening of one or more openings 28 may be precisely selected to permit blood to flow between the first and second atria responsive to a pressure gradient across the interatrial septum via the area of the opening of one or more openings 28, one or more openings 26, and the lumen of sheath 20 at a predetermined blood flow rate. Moreover, the selected area of the opening of one or more openings 28 corresponds with a specifically sized shunt, e.g., an interatrial shunt having a diameter at the passageway of the neck region of the shunt equal to, for example, 4 mm, 4.5 mm, 5 mm, 5.5 mm, 6 mm, 6.5 mm, 7 mm, 7.5 mm, or 8 mm. For simulating blood flow through larger interatrial shunts, e.g., having a diameter of greater than 7 mm, variations of the handle engagement may be used for larger diameter correlations. As will be understood by a person having ordinary skill in the art, the selected area of the opening of the one or more openings of the sheath may correspond to a diameter at the passageway of the neck region of the shunt, and is not limited to 0.5 mm increments.

Figure 4C:
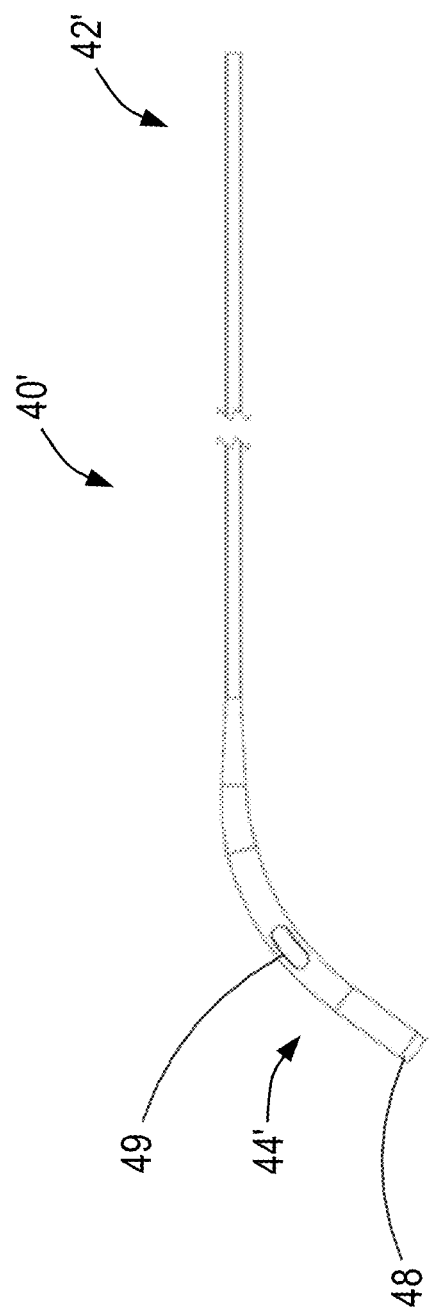
FIG. 4C illustrated an alternative exemplary inner sleeve constructed in accordance with the principles of the present invention.

Referring now to FIG. 4C, an alternative exemplary inner sleeve is provided. Inner sleeve 40' is constructed similarly to inner sleeve 40 of FIG. 4A wherein like components are identified by like-primed reference numbers. For example, proximal region 42' corresponds with proximal region 42, and distal region 44' corresponds with distal region 44. Inner sleeve 40' differs from inner sleeve 40 in that inner sleeve 40' has a first set of one or more apertures 48 at its distal end, and a second set of pre-cut features, e.g., one or more apertures 49 disposed along inner sleeve 40' at a position proximal to one or more apertures 48.

One or more apertures 49 are in fluid communication with one or more apertures 48 of inner sleeve 40' via a lumen of inner sleeve 40', and one or more apertures 48 is in fluid communication with one or more openings 26 of sheath 20 when inner sleeve 40' is positioned within the lumen of sheath 20, thereby permitting blood to flow between the first and second atria responsive to the pressure gradient across the interatrial septum via an opening between one or more openings 28 and one or more apertures 49, one or more openings 26, one or more apertures 48, and the inner sleeve's lumen and the sheath's lumen, depending on the amount of registration between one or more openings 28 and one or more apertures 49.

One or more apertures 49 are sized and shaped to register with one or more openings 28 of sheath 20. For example, inner sleeve 40' initially may be positioned within sheath 20 such that one or more apertures 49 and one or more openings 28 are not registered at all, thereby preventing blood from flowing through the opening of one or more openings 28 of sheath 20 as one or more openings 28 are completely obstructed by the body of inner sleeve 40'. Further, as inner sleeve 40' is moved proximally relative to sheath 20, the area of the opening between the lumen of inner sleeve 40' and the RA increases as one or more apertures 49 begin to register with one or more openings 28. As will be understood by a person having ordinary skill in the art, the direction of motion of inner sleeve 40' relative to sheath 20 required to register one or more openings 28 and one or more apertures 49 depends on the location of one or more openings 28 relative to one or more apertures 49. For example, if one or more openings 28 are positioned distal to one or more apertures 49 in the operation position, distal movement of inner sleeve 40' will permit registration of one or more openings 28 and one or more apertures 49.

Accordingly, blood is permitted to flow between the first and second atria responsive to a pressure gradient across the interatrial septum via the opening of one or more openings 28 created by the registration between one or more openings 28 and one or more apertures 49, one or more openings 26 of sheath 20, one or more apertures 48 of inner sleeve 40', and the lumens of sheath 20 and inner sleeve 40'. Inner sleeve 40' may be moved incrementally such that each selected position of inner sleeve 40' with respect to sheath 20 provides a predetermined area of the opening of one or more openings 28 corresponding with a specific interatrial shunt size. When one or more apertures 49 are completely registered with one or more openings 28, device 10 simulates blood flow through a maximum sized shunt, e.g., 8 mm.

Referring now to FIGS. 5A and 5B, an exemplary actuator is provided. Actuator 50 may be a handle sized and shaped to be easily controlled by the physician external to the patient's body, and includes very accurate mechanisms to control retraction or advancement of inner sleeve 40 within sheath 20. Actuator 50 is operatively coupled to the proximal regions of sheath 20 and inner sleeve 40 such that actuation of actuator 50 incrementally moves distal region 44 of inner sleeve 40 relative to distal region 24 of sheath 20. Shunted blood volume may be translated to effective shunt diameter by pre-set features on actuator 50. As shown in FIG. 5A, actuator 50 may include first actuator 52, e.g., a switch, and second actuator 54, e.g., a rotatable knob. First actuator 52 is operatively coupled to inner sleeve 40 such that actuation of first actuator 52, e.g., retraction of first actuator 52 relative to actuator 50, causes inner sleeve 40 to move a predetermined distance relative to sheath 20. For example, in the initial starting position, first actuator 52 is positioned at a distal portion of actuator 50 and serves as a dilator within sheath 20. Accordingly, inner sleeve 40 is positioned within sheath 20 such that blood is not permitted to flow through one or more openings 28 of sheath 20 due to obstruction of the opening of one or more openings 28 by inner sleeve 40.

First actuator 52 may then be moveable to a second operation position proximal to the initial starting position along actuator 50, thereby causing inner sleeve 40 to move a predetermined distance relative to sheath 20. In the second operation position, the distal end of inner sleeve 40 is positioned adjacent to one or more openings 28 of sheath 20, though not exposing any opening of one or more openings 28, and thus preventing blood to flow therethrough. Accordingly, upon actuation of first actuator 52, device 10 is ready to use. In addition, actuator 50 may include marker 56 for providing a visual indication to the physician of the current simulated shunt size.

Referring now to FIG. 5B, a cross-sectional view of actuator 50 along line A-A of FIG. 5A is illustrated. As shown in FIG. 5B, second actuator 54 may have threaded portion 58 corresponding to a threaded portion of actuator 50 such that rotation of second actuator 54 precisely and gradually moves inner sleeve 40 relative to sheath 20. Accordingly, the length of sheath 20 may be fixed relative to actuator 50, whereas the inner sleeve 40 moves proximally or distally relative to sheath 20 via actuation of second actuator 54 to expose or block one or more openings 28 of sheath 20. For example, after first actuator 52 is moved from the initial starting position to the second operation position, second actuator 54 may then be actuated to incrementally and gradually move inner sleeve 40 relative to sheath 20, thereby incrementally increasing the area of the opening of one or more openings 28 of sheath 28 to permit blood to flow therethrough.

Figure 6:
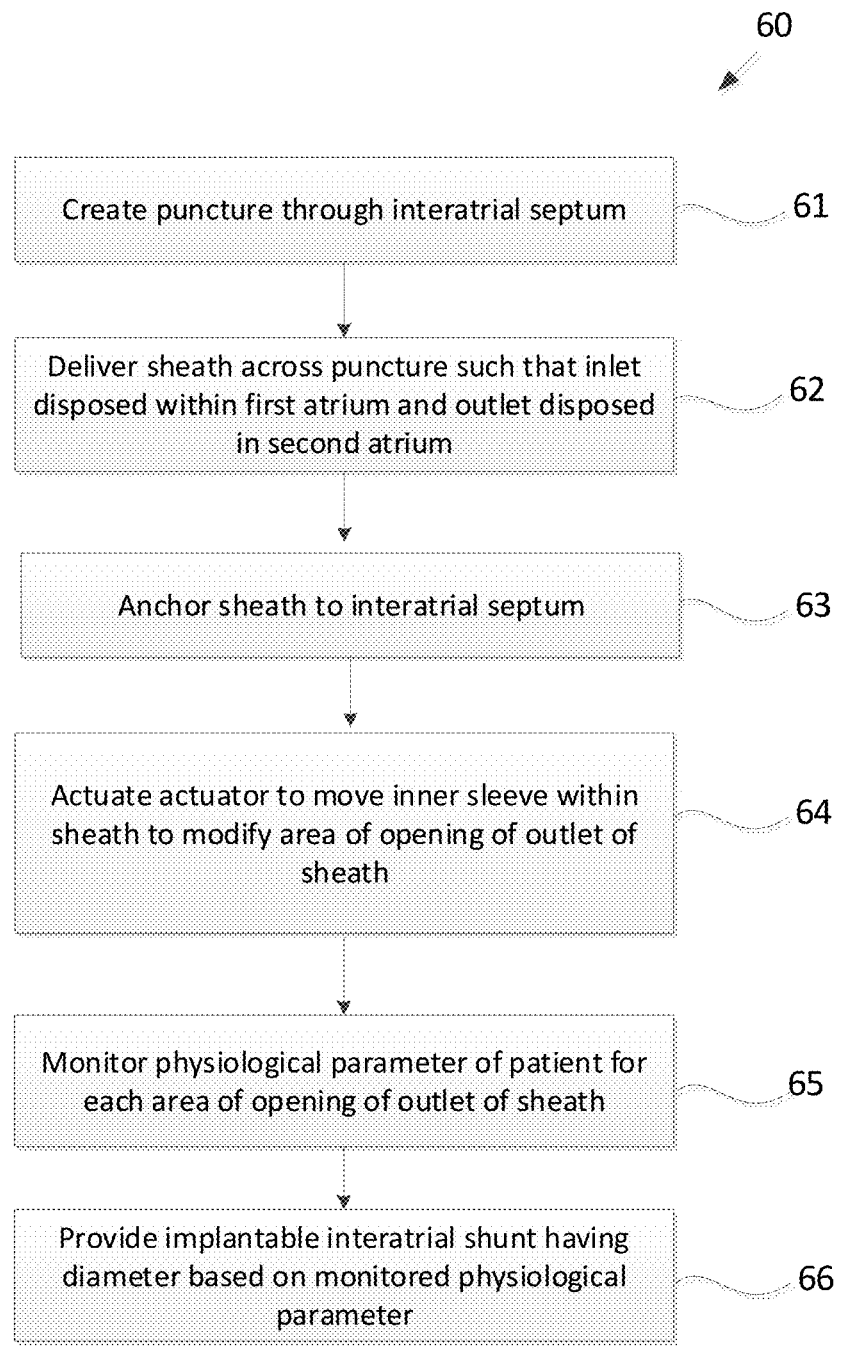
FIG. 6 is a flow chart of exemplary method steps for precise control of blood flow across a patient's interatrial septum in accordance with the principles of the present invention.

Referring now to FIG. 6, the steps of exemplary method 60 of using device 10 of FIG. 1A for precise control of blood flow across a patient's interatrial septum in accordance with the principles of the present invention are provided. Some of the steps of method 60 may be further elaborated by referring to FIGS. 7A-7I. In addition, for purposes of discussion below, method 60 will be described for precise control of blood flow from the patient's right atrium, across the interatrial septum to the patient's left atrium, e.g., to treat PAH; however, as will be understood by a person having ordinary skill in the art, method 60 may be used for precise control of blood flow from the patient's left atrium, across the interatrial septum to the patient's right atrium, e.g., to treat LVHF, depending on the pressure gradient across the interatrial septum. Moreover, method 60 may be used to facilitate blood flow from one heart chamber to another heart chamber.

At step 61, a puncture is created through the patient's interatrial septum, e.g., through the patient's fossa ovalis, using techniques known in the art such as those described in U.S. Pat. No. 9,713,696 to Yacoby, the entire contents of which is incorporated by reference herein. Accordingly, a guidewire may be delivered across the puncture of the interatrial septum, and at step 62, sheath 20 is delivered over the guidewire and across the puncture of the interatrial septum such that one or more openings 26 are disposed within a first atrium, e.g., the left atrium, and one or more openings 28 are disposed within the second atrium, e.g., the right atrium, as shown in FIG. 7A. Inner sleeve 40 is disposed within the lumen of sheath 20 such that inner sleeve 40 serves as a dilator, and sheath 20 and inner sleeve 40 are advanced over the guidewire via guidewire lumen 47 of inner sleeve 40. Metal coil 31 may be used to emit RF energy to heat the tissue contouring the puncture of the interatrial septum, to thereby ablate the tissue and alter tissue healing to prevent or limit proliferate tissue in growth in response to mechanical injury.

At step 63, sheath 20 may optionally be anchored to the interatrial septum, such as by inflating balloon 30 within the left atrium, thereby preventing proximal movement of sheath 20 with respect to the patient's interatrial septum, as shown in FIG. 7B. As described above, different shaped balloons may be used to secure sheath 20 within the puncture of the interatrial septum. For example, the balloon may have a dog-bone shape such that the waist of the balloon contacts the contour of the puncture of the interatrial septum while the opposing sides of the balloon are inflated to sandwich the interatrial septum therebetween. Accordingly, metal coil 31 may be disposed on the waist of the balloon, and actuated to emit RF energy to ablate the surrounding tissue to alter tissue healing adjacent the waist of the balloon. When sheath 20' is used, step 63 may be skipped and/or other means of anchoring the sheath may be deployed. In addition, as described above, alternative or additional septal fixation elements, e.g., deployable tines, may be used to anchor sheath 20 to the interatrial septum.

Figure 7C:
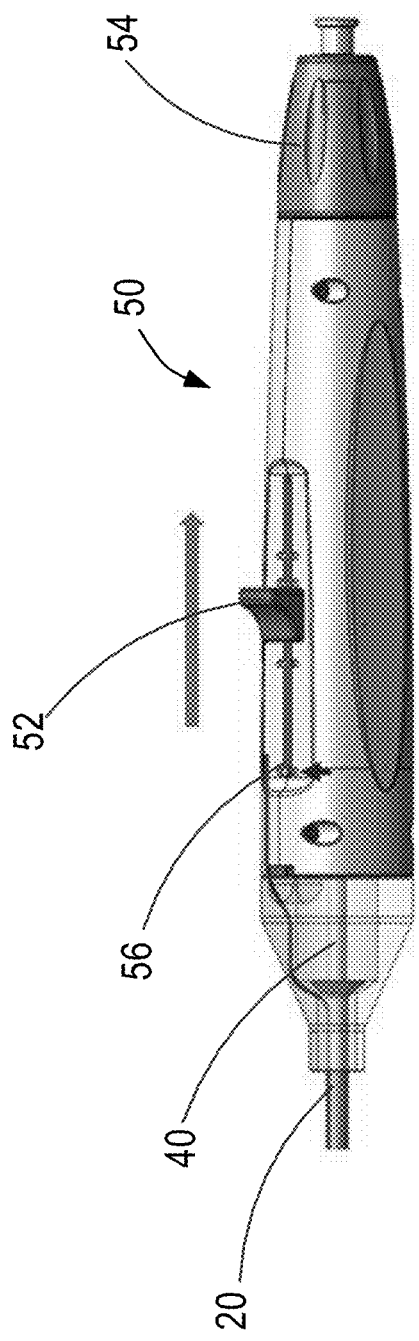
Figure 7D:
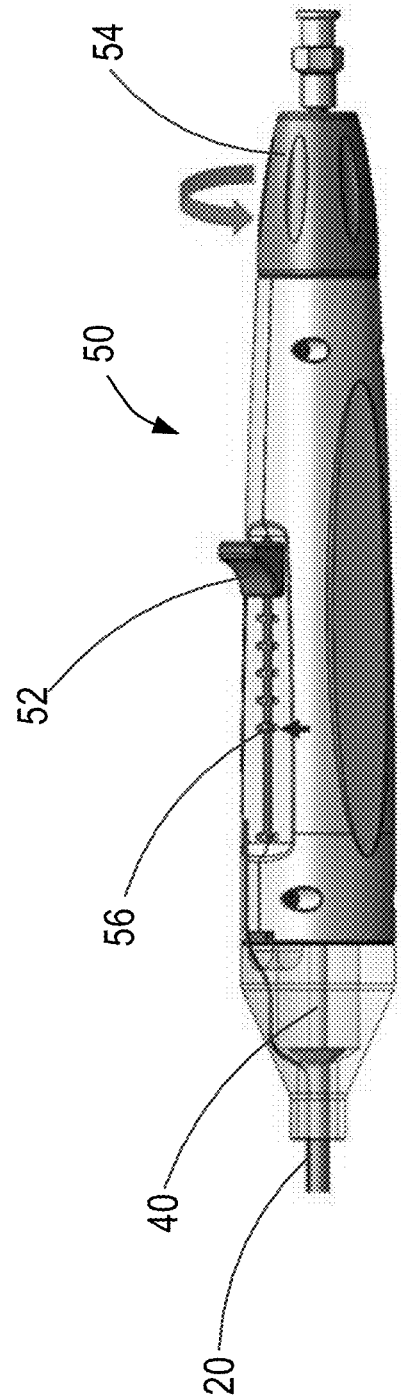

At step 64, actuator 50 is actuated to move inner sleeve 40 proximally within sheath 20 to modify the area of the opening of one or more openings 28 of sheath 20. For example, as shown in FIG. 7C, first actuator 52 may be moved from the initial starting position proximally to the second operation position. When first actuator 52 is in the second operation position, second actuator 54 may then be actuated to incrementally move inner sleeve 40 with respect to sheath 20 as shown in FIG. 7D. Specifically, FIG. 7D illustrates when second actuator 54 has been rotated such that marker 56 moves from an initial position indicating complete obstruction of one or more openings 28 and thus, no blood flows from the right atrium through one or more openings 28 into the left atrium, to a position along actuator 50 indicating the minimum opening of one or more openings 28 to permit blood flow therethrough corresponding to, e.g., a 4 mm interatrial shunt. In addition, first actuator 52 may also function as a safety lock such that second actuator 54 may not be actuated until first actuator 52 is actuated to the second operation position.

Accordingly, second actuator 54 may then be actuated to incrementally move inner sleeve 40 relative to sheath 20 as illustrated in FIGS. 7E to 7G. For example, as shown in FIG. 7E, second actuator 54 may be rotated until marker 56 indicates that the area of the opening of one or more openings 28 permits blood to flow therethrough between the right and left atria at a blood flow rate corresponding with blood flow through a 4.5 mm interatrial shunt. As shown in FIG. 7F, second actuator 54 may be further rotated until marker 56 indicates that the area of the opening of one or more openings 28 permits blood to flow therethrough between the right and left atria at a blood flow rate corresponding with blood flow through a 5 mm interatrial shunt. As shown in FIG. 7G, second actuator 54 may further be rotated until marker 56 indicates that the area of the opening of one or more openings 28 permits blood to flow therethrough between the right and left atria at a blood flow rate corresponding with blood flow through a 5.5 mm interatrial shunt. As will be understood by a person having ordinary skill in the art, actuator 50 may be actuated to simulate blood flow through smaller or larger interatrial shunts, e.g., a 3.5 mm shunt, a 6 mm shunt, a 6.5 mm shunt, a 7 mm shunt, a 7.5 mm shunt, and an 8 mm shunt, etc.

As described above, the area of the opening of one or more openings 28 may be measured as the space between one or more openings 28 and the body of inner sleeve 40, or the registered space between one or more openings 28 of sheath 20 and one or more apertures 49 of inner sleeve 40'. In addition, the decision of which sized shunt to select for the patient may be based on a conversion lookup table derived from comparative in vitro bench tests or in-vivo experiments.

Moreover, at step 65, the patient's hemodynamics may be monitored by measuring the patient's physiological parameters at each incremental area of the opening of one or more openings 28 during operation of device 10. For example, one or more sensors 21 may measure one or more physiological parameters including at least one of pressure, blood flow rate, blood flow velocity, or oximetry, to determine to effectiveness of the therapy, e.g., on interatrial pressures, cardiac output, blood saturation, etc. Sensors 21 may further generate a signal(s) indicative of the measured physiological parameters for transmission to external controller 55 for monitoring. Alternatively, or additionally, the guidewire used to deliver sheath 20 and inner sleeve 40 may be a pressure sensor guidewire operatively coupled to external controller 55 for measuring pressure within the first atrium and generating a signal indicative of the measured pressure for transmission to external controller 55. Accordingly, external controller 55 may compare the measured physiological parameters with stored desired threshold values and display such results such that a physician may determine which sized shunt is best suited for each individual patient.

Figure 7H:
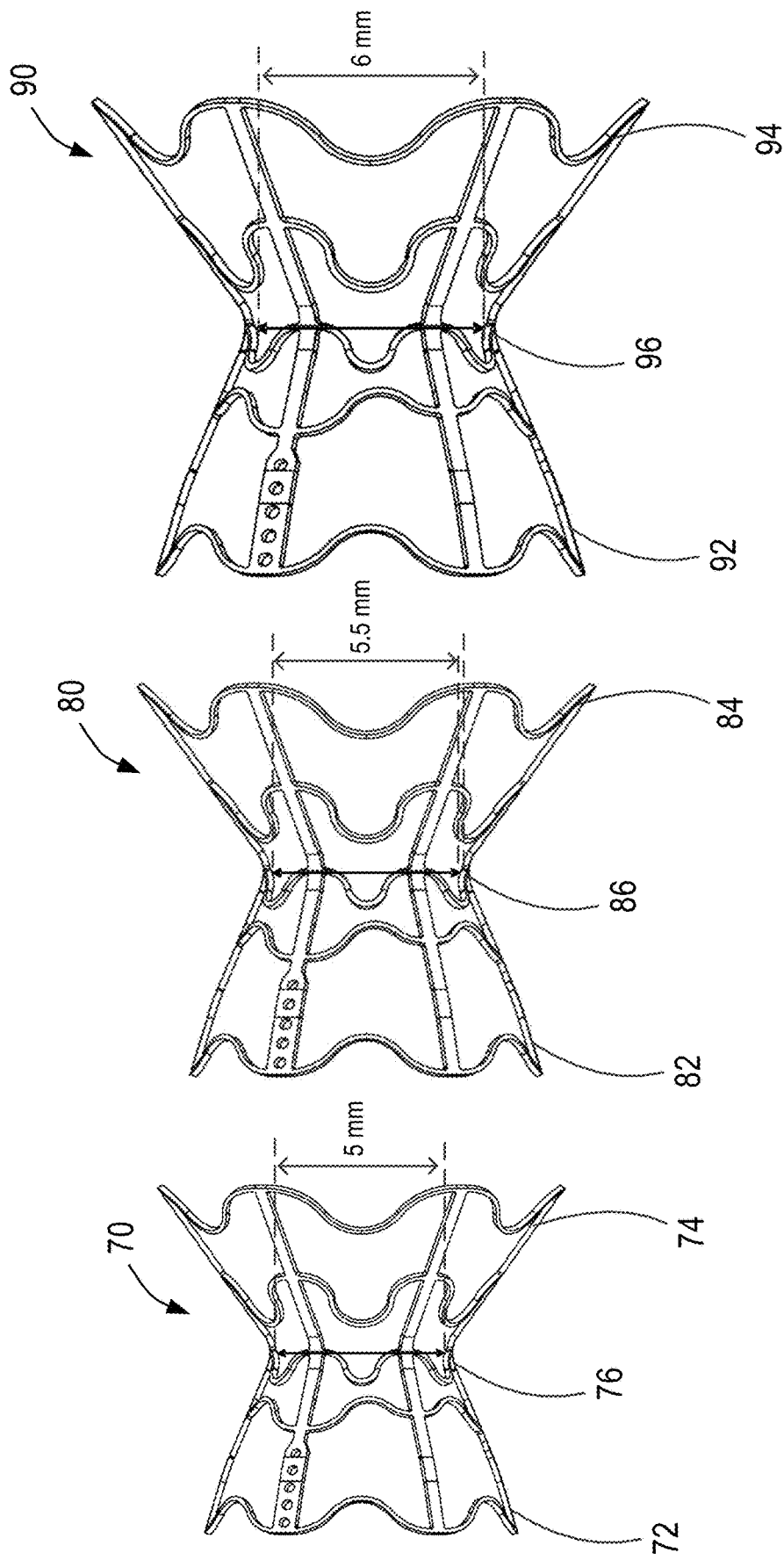
Figure 71:
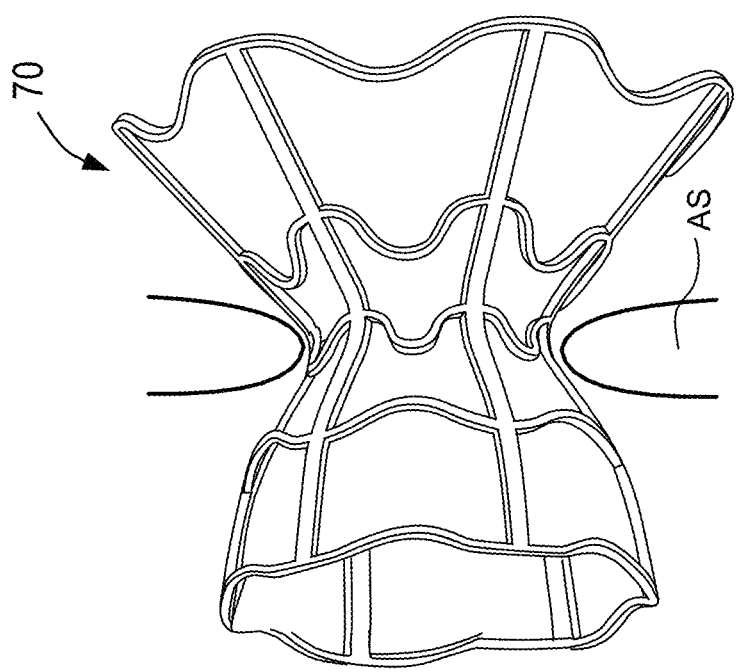

At step 66, the physician selects a specifically sized interatrial shunt to be implanted within the puncture of the specific patient's interatrial septum based on the patient's monitored hemodynamics responsive to each actuated increment of actuator 50. For example, as shown in FIG. 7H, the physician may select between shunt 70 having a 5 mm diameter at neck region 76 between first region 72 and second region 74, shunt 80 having a 5.5 mm diameter at neck region 86 between first region 82 and second region 84, and shunt 90 having a 6 mm diameter at neck region 96 between first region 92 and second region 94 for implantation within the patient. As will be understood by a person having ordinary skill in the art, smaller or larger interatrial shunts may be selected for implantation including, e.g., a 4.5 mm shunt, a 6.5 mm shunt, a 7 mm shunt, a 7.5 mm shunt, or an 8 mm shunt. Accordingly, the selected interatrial shunt, e.g., shunt 70, may then be implanted within the patient's interatrial septum AS, as shown in FIG. 7I, via methods and delivery tools as described in, e.g., U.S. Pat. No. 8,091,556 to Keren, U.S. Pat. No. 9,713,696 to Yacoby, U.S. Pat. No. 10,076,403 Eigler, the entire contents of each of which are incorporated by reference herein. Alternatively, sheath 20 and inner sleeve 40 may be detached from actuator 50 and kept in the patient's body for a period of time, as may be required, until removal.

EXPERIMENTAL RESULTS

The testing described in this section was conducted on an hourglass-shaped interatrial shunt (manufactured by V-Wave, Ltd, Caesarea, Israel), and a sheath-shunt prototype device under Steady Forward Flow test conditions. The purpose of this test was to compare the flow rates passing through 5 mm and 6 mm interatrial shunts and demonstrate how these correlate with flow rates passing through two corresponding settings on the actuator of the sheath-shunt prototype device. As demonstrated Table 2 below, there is good correlation between the two, with deviations ranging from 1% to 10% in maximum at various interatrial pressure gradient conditions.

TABLE 2

| ΔP [mm Hg] | Flow [ml/min] | | | Flow [ml/min] | | |
|---|---|---|---|---|---|---|
| | 5 mm Shunt | Sheath | Error [%] | 6 mm Shunt | Sheath | Error [%] |
| 6 | 1212 | 1316 | 8.5 | 1600 | 1621 | 1.3 |
| | 1287 | 1330 | 3.3 | 1717 | 1753 | 2.1 |
| 8 | 1360 | 1430 | 5.1 | 1910 | 1851 | 3.1 |
| | 1395 | 1445 | 3.5 | 1959 | 1911 | 2.4 |
| 10 | 1525 | 1682 | 10.2 | 2100 | 2045 | 2.6 |
| | 1554 | 1692 | 8.8 | 2170 | 2135 | 1.6 |
| 12 | 1765 | 1844 | 4.4 | 2269 | 2198 | 3.1 |
| | 1790 | 1879 | 4.9 | 2328 | 2277 | 2.1 |

Figure 8:
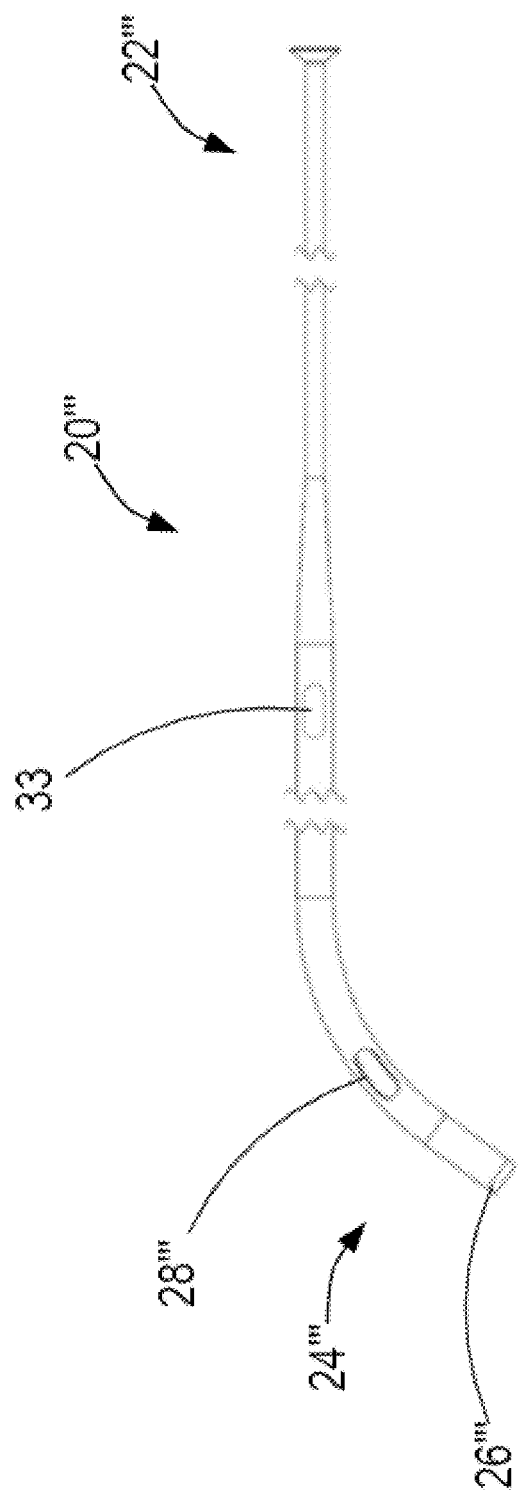
FIG. 8 illustrates another alternative exemplary sheath constructed in accordance with the principles of the present invention.

In accordance with another aspect of the present invention, the sheath may include three sets of one or more openings as shown in FIG. 8.

Sheath 20''' of FIG. 8 is constructed similarly to sheath 20 of FIG. 2A wherein like components are identified by like-triple primed reference numbers. For example, proximal region 22''' corresponds with proximal region 22, distal region 24''' corresponds with distal region 24, one or more openings 26''' corresponds with one or more openings 26, and one or more openings 28''' correspond with one or more openings 28. Sheath 20''' differs from sheath 20 in that sheath 20''' includes third set of one or more openings 33.

Third set of one or more openings 33 may be positioned on sheath 20''' at a location spaced apart from first and second set of one or more openings 26''', 28'''' such that when second set of one or more openings 28''' is disposed within the right atrium, third set of one or more openings 33 is disposed within the inferior vena cava above the patient's renal veins. Accordingly, upon further retraction of the inner sleeve, third set of one or more openings 33 may be exposed while second set of one or more openings 28''' are blocked, thereby permitting blood to flow via third set of one or more openings 33 and not second set of one or more openings 28''' responsive to the pressure gradient between the inferior vena cava and the left atrium. This may be accomplished by using an inner sleeve constructed similar to inner sleeve 40' having a first set of one or more apertures in fluid communication with first set of one or more openings 26''' of sheath 20''', a second set of one or more apertures sized and shaped to register with the sheath's second set of one or more openings 28''', and a third set of one or more apertures sized and shaped to register with the sheath's third set of one or more openings 33.

For example, when second set of one or more openings 28''' of sheath 20''' completely register with the second set of one or more apertures of the inner sleeve, third set of one or more openings 33 of sheath 20''' do not register at all with the third set of one or more apertures of the inner sleeve, and when second set of one or more openings 28''' of the sheath do not register at all with the first set of one or more apertures of the inner sleeve, third set of one or more openings 33 of the sheath 20''' registers with the third set of one or more apertures of the inner sleeve.

The second and third set of one or more apertures of the inner sleeve may be spaced apart a sufficient distance such that blood enters only via second set of one or more openings 28''' or third set of one or more openings 33 of sheath 20''' at a time. Since the venous return from the inferior vena cava is relatively enriched with oxygen because of less oxygen extraction by the kidneys, this source of shunted blood will cause a smaller fall in systemic oxygen saturation than a similarly sized shunt originating from the second set of one or more openings. This may be more advantageous for treating acute RV decompensation.

Figure 9:
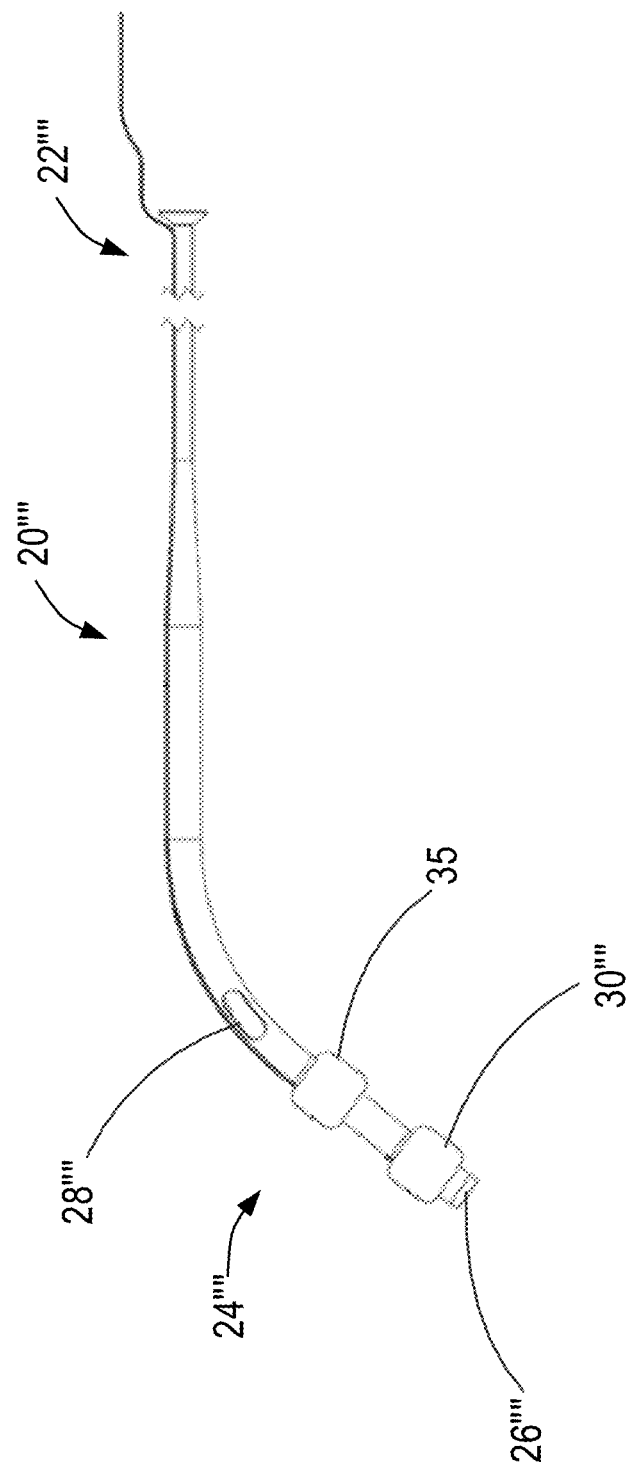
FIG. 9 illustrates another alternative exemplary sheath having two anchors constructed in accordance with the principles of the present invention.

Referring now to FIG. 9, an alternative exemplary sheath having dual anchors is provided. Sheath 20'''' is constructed similarly to sheath 20 of FIG. 2A wherein like components are identified by like-quadruple primed reference numbers. For example, proximal region 22'''' corresponds with proximal region 22, distal region 24'''' corresponds with distal region 24, one or more openings 26'''' correspond with one or more openings 26, one or more openings 28'''' correspond with one or more openings 28, and balloon 30'''' corresponds with balloon 30. Sheath 20'''' differs from sheath 20 in that sheath 20'''' includes second balloon 35 disposed on distal region 24'''' of sheath 20'''' proximal to balloon 30''''. Accordingly, balloon 35 may be inflated such that balloon 35 is positioned entirely within the patient's right atrium, and balloon 30'''' may be inflated such that balloon 30'''' is positioned entirely within the patient's left atrium, and thus, inflated balloons 30'''' and 35 may sandwich the interatrial septum for improved fixation, preventing both proximal and distal movement relative to the atrial septum. As will be understood by a person of ordinary skill in the art, like balloon 30 of FIG. 2A, balloon 30'''' and/or balloon 35 may have metal coils disposed thereon.

Figure 10:
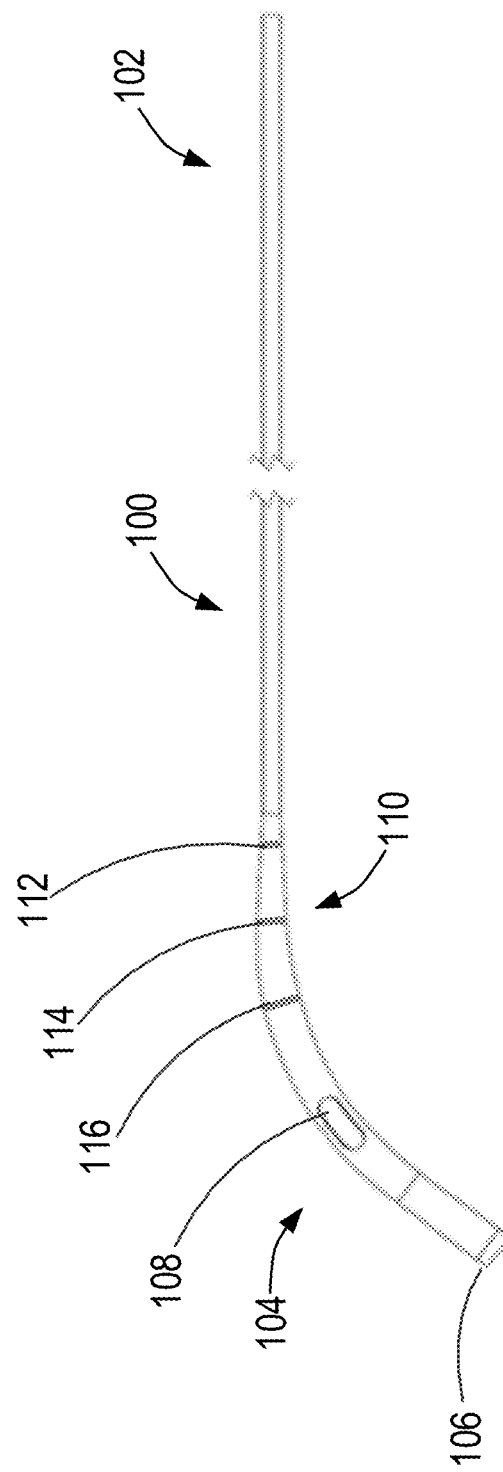
FIG. 10 illustrates another alternative exemplary sheath having a graded portion constructed in accordance with the principles of the present invention.

Referring now to FIG. 10, another alternative exemplary sheath having a graded portion is provided. Sheath 100 is constructed similarly to sheath 20' of FIG. 2B. For example, proximal region 102 corresponds with proximal region 22', distal region 104 corresponds with distal region 24', one or more openings 106 correspond with one or more openings 26', and one or more openings 108 correspond with one or more openings 28'. Sheath 100 differs from sheath 20' in that sheath 100 has graded portion 110 in the vicinity of distal region 104. As shown in FIG. 10, graded portion 110 may be positioned at a predetermined distance proximal to one or more openings 108, e.g., 1-4 cm, such that when graded portion 110 is disposed in the puncture of the interatrial septum, distal region 104 of sheath 100 does not extend too far within the left atrium.

Moreover, one or more metal coils, e.g., metal coils 112, 114, and 116, may be disposed on the outer surface of graded portion 110 of sheath 100 at preselected positions along graded portion 110 corresponding with predetermined interatrial shunt sizes. For example, the cross-sectional area of sheath 100 at graded portion 110 may decrease in the direction from distal region 104 toward proximal region 102, and metal coil 112 may be positioned on graded portion 110 corresponding with, e.g., a 5 mm diameter interatrial shunt, metal coil 114 may be positioned on graded portion 110 corresponding with, e.g., a 5.5 mm diameter interatrial shunt, and metal coil 116 may be positioned on graded portion 110 corresponding with, e.g., a 6 mm diameter interatrial shunt.

Thus, after the physician determines which sized shunt is best suited for a patient using the systems and methods described herein, sheath 100 may be moved distally through the puncture of the interatrial septum until the interatrial septum aligns within any one of metal coils 112, 114, or 116. Accordingly, the puncture of the interatrial septum conforms to the cross-sectional area of graded portion 110 positioned therethrough, and the respective metal coil may be actuated to emit RF energy to ablate tissue adjacent to the metal coil to induce an interatrial shunt having a size corresponding to the cross-sectional area of graded portion 110. For example, if the interatrial septum is aligned with metal coil 112, ablation of the interatrial tissue surrounding metal coil 112 via metal coil 112 will result in a puncture sized to receive interatrial shunt 70 of FIG. 7H. Similarly, if the interatrial septum is aligned with metal coil 114, ablation of the interatrial tissue surrounding metal coil 114 via metal coil 114 will result in a puncture sized to receive interatrial shunt 80 of FIG. 7H, and if the interatrial septum is aligned with metal coil 116, ablation of the interatrial tissue surrounding metal coil 116 via metal coil 116 will result in a puncture sized to receive interatrial shunt 90 of FIG. 7H. As will be understood by a person having ordinary skill in the art, there may be less or more than three metal coils disposed along the length of graded portion 110, and/or graded portion 110 may have a geometry such that the metal coils disposed thereon induce interatrial shunts of sizes less 5 mm or greater than 6 mm, e.g., 6.5 mm, 7 mm, 7.5 mm, 8 mm, etc. In addition, any of the sheaths described herein, e.g., sheath 20, sheath 20', sheath 20'', sheath 20''', or sheath 20'''', may include a graded portion similar to graded portion 110.

In one embodiment, instead of graded portion 110, the sheath may have a hot balloon disposed thereon proximal to the one or more openings configured to be disposed in the patient's left atrium, such that after the physician determines which sized shunt is best suited for a patient using the systems and methods described herein, sheath 100 may be moved distally through the puncture of the interatrial septum until the interatrial septum aligns with the metal coils on the hot balloon. The hot balloon may then be inflated to a selected size to thereby expand the puncture of the interatrial septum to a size corresponding with the desired shunt size. The hot balloon may then be actuated to ablate the tissue of the interatrial septum surrounding the hot balloon to induce the desired interatrial shunt, such that the desired interatrial shunt may be implanted within the ablated puncture.

In accordance with another aspect of the present invention, the sheath may include two sets of one or more openings, e.g., a first set of one or more openings positioned at the distal region of the sheath such that they are positioned within the patient's left atrium, and a second set of one or more openings positioned on the sheath at a location spaced apart from the first set of one or more openings such that when the first set of one or more openings is disposed within the left atrium, the second set of one or more openings is disposed within the inferior vena cava just caudal of the patient's renal veins during operation. Accordingly, an inner sleeve having corresponding first and second sets of one or more apertures may be actuated to modify the area of the opening of the second set of one or more openings of the sheath to permit blood to flow between the inferior vena cava and the left atrium responsive to a pressure gradient between the inferior vena cava and the left atrium in accordance with the principles of the present invention described above. For example, when the sheath is intended to provide right to left flow, as in PAH, there would be a reduced flow compared to the shorter flow path through the sheaths between the RA and LA, which may be accounted for during calibration of the system.

While various illustrative embodiments of the invention are described above, it will be apparent to one skilled in the art that various changes and modifications may be made herein without departing from the invention. It will further be appreciated that the devices described herein may be implanted in other positions in the heart. For example, device 10 may be similarly used for treating conditions in which the distal chamber (LA) pressure is higher than the proximal chamber (RA) pressure, as occurs in patients with congestive heart failure. In such cases, the flow will be in the direction from the left atrium to the right atrium. There are small, e.g., approximately 10%, differences in calibrated effective flow diameters between forward and reverse flow, which may be allowed for by providing separate calibrations on the actuator. In addition, device 10 may be implanted across the ventricular septum, in an orientation suitable to shunt blood between the left ventricle and the right ventricle, depending on the pressure gradient between the left and right ventricles. The appended claims are intended to cover all such changes and modifications that fall within the true spirit and scope of the invention.

What is claimed:

1. A device for control of blood flow across a patient's interatrial septum, the device comprising:
    a sheath having a proximal region configured to extend external to the patient's body, a distal region configured to be disposed across the patient's interatrial septum, and a lumen therebetween, the distal region having a first set of one or more openings and a second set of one or more openings spaced apart from the first set of one or more openings a distance greater than a thickness of the interatrial septum such that the first set of one or more openings is configured to be disposed within a first atrium of the patient while the second set of one or more openings is disposed in a second atrium of the patient; and
    an actuator operatively coupled to the proximal region of the sheath, the actuator configured to be selectively actuated to modify an area of an opening of the second set of one or more openings of the sheath, such that blood is permitted to flow between the first and second atria responsive to a pressure gradient across the interatrial septum via the first and second sets of one or more openings and the sheath lumen therebetween, at a blood flow rate corresponding with the area of the opening of the second set of one or more openings of the sheath.

2. The device of claim 1, wherein the second set of one or more openings of the sheath comprise at least one of a circular, elliptical, or elongated slot shape, or any combination thereof.

3. The device of claim 1, wherein the second set of one or more openings of the sheath is distributed symmetrically about an outer surface of the sheath.

4. The device of claim 1, wherein the second set of one or more openings of the sheath is distributed asymmetrically about an outer surface of the sheath.

5. The device of claim 1, further comprising:
    an inner sleeve having a proximal region and a distal region having an outer diameter equal to an inner diameter of the sheath, the inner sleeve moveably disposed within the lumen of the sheath,
    wherein the actuator is configured to be selectively actuated to modify the area of the opening of the second set of one or more openings of the sheath by moving the inner sleeve relative to the sheath by an incremental amount such that blood is permitted to flow between the first and second atria responsive to a pressure gradient across the interatrial septum via the first and second sets of one or more openings and the sheath lumen therebetween, at a blood flow rate corresponding with the area of the opening of the second set of one or more openings of the sheath.

6. The device of claim 5, wherein the inner sleeve further comprises one or more flushing ports in fluid communication with a source of flushing fluid via one or more flushing lumens of the inner sleeve, the one or more flushing ports configured to eject the flushing fluid therethrough to prevent accumulation of blood clots at the second set of one or more openings of the sheath.

7. The device of claim 5, wherein the inner sleeve comprises a guidewire lumen sized and shaped for receiving a guidewire.

8. The device of claim 7, further comprising a pressure sensor guidewire configured to be disposed within the guidewire lumen of the inner sleeve, the pressure sensor guidewire operatively coupled to an external controller and configured to measure pressure within the first atrium and to transmit a signal indicative of the measured pressure to the external controller.

9. The device of claim 1, further comprising:
    an inner sleeve having a proximal region, a distal region having a first set of one or more apertures in fluid communication with the first set of one or more openings of the sheath, and a lumen extending therebetween, the inner sleeve moveably disposed within the lumen of the sheath and comprising a second set of one or more apertures sized and shaped to register with the second set of one or more openings of the sheath,
    wherein the actuator is configured to be selectively actuated to modify the area of the opening of the second set of one or more openings of the sheath by moving the inner sleeve relative to the sheath to register the second set of one or more apertures of the inner sleeve with the second set of one or more openings of the sheath by a predetermined amount such that blood is permitted to flow between the first and second atria responsive to a pressure gradient across the interatrial septum via the first and second sets of one or more openings and apertures and the inner sleeve lumen therebetween, at a blood flow rate corresponding with the predetermined amount of registration between the second set of one or more apertures of the inner sleeve and the second set of one or more openings of the sheath.

10. The device of claim 9, wherein the sheath further comprises a third set of one or more openings spaced apart from the second set of one or more openings such that the third set of one or more openings is configured to be disposed within an inferior vena cava of the patient while the first set of one or more openings is disposed in the first atrium, wherein the inner sleeve further comprises a third set of one or more apertures sized and shaped to register with the third set of one or more openings of the sheath, and wherein the actuator is further configured to be selectively actuated to move the inner sleeve relative to the sheath to register the third set of one or more apertures of the inner sleeve with the third set of one or more openings of the sheath by a predetermined amount such that blood is permitted to flow between the inferior vena cava and the first atrium responsive to a pressure gradient between the inferior vena cava and the first atrium via the first and third sets of one or more openings and apertures and the inner sleeve lumen therebetween.

11. The device of claim 10, wherein, when the third set of one or more apertures completely register with the third set of one or more openings, the second set of one or more apertures of the inner sleeve are not registered with the second set of one or more openings of the sheath.

12. The device of claim 1, wherein the actuator is configured to be selectively actuated to incrementally select the area of the opening of the second set of one or more openings of the sheath, such that the blood flow rate of the blood flow between the first and second atria to the at each increment corresponds with a blood flow rate of blood flow through a predetermined sized interatrial shunt implanted within the patient's interatrial septum.

13. The device of claim 12, wherein the area of the opening of the second set of one or more openings of the sheath corresponds with the blood flow rate of blood flow through the predetermined sized interatrial shunt having a diameter between 4 to 8 mm.

14. The device of claim 1, further comprising one or more sensors disposed within the lumen of the sheath and operatively coupled to an external controller, the one or more sensors configured to measure one or more physiological parameters and to transmit a signal indicative of the measured physiological parameter to the external controller.

15. The device of claim 14, wherein the one or more physiological parameters comprise at least one of pressure, blood flow rate, blood flow velocity, or oximetry.

16. The device of claim 1, further comprising an anchor disposed at the distal region of the sheath, the anchor configured to facilitate fixation of the sheath to the patient's interatrial septum.

17. The device of claim 16, wherein the anchor comprises a balloon, configured to prevent movement of the sheath relative to the patient's interatrial septum.

18. The device of claim 17, wherein the balloon is configured to be inflated within the first atrium, thereby preventing proximal movement of the sheath relative to the patient's interatrial septum.

19. The device of claim 18, further comprising a second balloon configured to be inflated within the second atrium, wherein the first and second balloons, when inflated, sandwich the interatrial septum.

20. The device of claim 17, wherein the balloon is configured to be inflated within the second atrium, thereby preventing distal movement of the sheath relative to the patient's interatrial septum.

21. The device of claim 17, wherein the balloon comprises a metal coil disposed on its outer surface, the metal coil configured to emit RF energy sufficient to ablate tissue adjacent to the metal coil.

22. The device of claim 16, wherein the anchor comprises deployment tines.

23. The device of claim 1, further comprising a metal coil disposed on an outer surface of the sheath, the metal coil configured to emit RF energy sufficient to ablate tissue adjacent to the metal coil to induce an interatrial shunt.

24. The device of claim 23, wherein the metal coil is disposed on the outer surface of the sheath proximal to the second set of one or more openings.

25. The device of claim 23, further comprising one or more additional metal coils, wherein each of the metal coils are configured to emit RF energy sufficient to ablate tissue adjacent to the respective metal coil to induce an interatrial shunt having a predetermined diameter.

26. The device of claim 25, wherein a graded portion of the sheath comprises an outer surface having a cross-sectional area that increases in a distal direction, each of the metal coils disposed along the graded portion of the sheath at a position corresponding the predetermined diameter.

27. A method for controlling of blood flow across a patient's interatrial septum, the method comprising:
creating a puncture through the patient's interatrial septum;
delivering a sheath across the puncture such that a first set of one or more openings of the sheath is disposed within a first atrium of the patient a second set of one or more openings of the sheath is disposed within a second atrium of the patient, and a proximal region of the sheath extends external to the patient's body;
permitting blood to flow between the first and second atria responsive to a pressure gradient across the interatrial septum via the first and second set of one or more openings and a lumen of the sheath;
modifying an area of an opening of the second set of one or more openings by selectively actuating an actuator operatively coupled to the proximal region of the sheath, such that blood is permitted to flow between the first and second atria via the first and second set of one or more openings and a lumen of the sheath at a modified blood flow rate; and
selecting an interatrial shunt for implantation in the patient's interatrial septum based on the modified area of the opening of the second set of one or more openings.

* * * * *